(12) United States Patent
Alvaro et al.

(10) Patent No.: US 9,833,452 B2
(45) Date of Patent: *Dec. 5, 2017

(54) COMPOUNDS

(71) Applicant: AUTIFONY THERAPEUTICS LIMITED, London (GB)

(72) Inventors: Giuseppe Alvaro, Verona (IT); Agostino Marasco, Verona (IT)

(73) Assignee: AUTIFONY THERAPEUTICS LIMITED, Hertfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,465

(22) Filed: Jul. 11, 2016

(65) Prior Publication Data

US 2016/0317537 A1    Nov. 3, 2016

Related U.S. Application Data

(60) Continuation of application No. 14/816,476, filed on Aug. 3, 2015, now Pat. No. 9,422,272, which is a division of application No. 14/361,510, filed as application No. PCT/GB2012/053045 on Dec. 6, 2012, now Pat. No. 9,133,175.

(30) Foreign Application Priority Data

Dec. 6, 2011  (GB) ................. PCT/GB2011/052414

(51) Int. Cl.
| | |
|---|---|
| *C07D 405/14* | (2006.01) |
| *A61K 31/506* | (2006.01) |
| *C07D 405/12* | (2006.01) |
| *C07D 413/12* | (2006.01) |
| *C07D 413/14* | (2006.01) |
| *C07D 307/79* | (2006.01) |
| *C07D 307/94* | (2006.01) |
| *C07D 317/46* | (2006.01) |
| *A61K 31/4439* | (2006.01) |

(52) U.S. Cl.
CPC ........ *A61K 31/506* (2013.01); *A61K 31/4439* (2013.01); *C07D 307/79* (2013.01); *C07D 307/94* (2013.01); *C07D 317/46* (2013.01); *C07D 405/12* (2013.01); *C07D 405/14* (2013.01); *C07D 413/12* (2013.01); *C07D 413/14* (2013.01)

(58) Field of Classification Search
CPC ............... C07D 405/14; C07D 413/14; A61K 31/4178; A61K 31/4439; A61K 31/506
USPC ............... 544/316; 546/274.1; 514/274, 337
See application file for complete search history.

(56) References Cited

U.S. PATENT DOCUMENTS

| | | | |
|---|---|---|---|
| 4,350,701 A | 9/1982 | Costin et al. | |
| 4,675,403 A | 6/1987 | Abou-Gharbia et al. | |
| 4,804,671 A | 2/1989 | Costin et al. | |
| 5,362,878 A | 11/1994 | Chang et al. | |
| 5,656,634 A | 8/1997 | Chang et al. | |
| 5,703,087 A | 12/1997 | Perregaard et al. | |
| 9,133,175 B2 | 9/2015 | Alvaro | |
| 9,346,790 B2 * | 5/2016 | Alvaro | C07D 405/12 |
| 9,422,272 B2 * | 8/2016 | Alvaro | C07D 405/12 |
| 2003/0008884 A1 | 1/2003 | Gerusz et al. | |
| 2003/0149061 A1 | 8/2003 | Nishihara et al. | |
| 2005/0009817 A1 | 1/2005 | Savoy et al. | |
| 2005/0153968 A1 | 7/2005 | Bi et al. | |
| 2007/0004753 A1 | 1/2007 | Sawyers et al. | |
| 2007/0254933 A1 | 11/2007 | Jung et al. | |
| 2008/0139634 A2 | 6/2008 | Jung et al. | |
| 2008/0261961 A1 | 10/2008 | Flynn et al. | |
| 2010/0158860 A1 | 6/2010 | Steiner | |
| 2010/0172975 A1 | 7/2010 | Sawyers et al. | |
| 2010/0210665 A1 | 8/2010 | Sawyers et al. | |
| 2011/0003839 A1 | 1/2011 | Jung et al. | |
| 2011/0123490 A1 | 5/2011 | Schoenfeld et al. | |
| 2012/0190718 A1 | 7/2012 | Jung et al. | |
| 2012/0289526 A1 | 11/2012 | Alvaro et al. | |
| 2014/0323508 A1 | 10/2014 | Alvaro | |
| 2015/0336936 A1 | 11/2015 | Alvaro et al. | |

FOREIGN PATENT DOCUMENTS

| | | |
|---|---|---|
| DE | 3836175 | 5/1990 |
| EP | 0368008 | 5/1990 |
| EP | 0726898 | 12/2000 |
| EP | 1206935 | 5/2002 |
| GB | 2216890 | 10/1989 |
| WO | 91/04027 | 4/1991 |
| WO | 96/36229 | 11/1996 |
| WO | 96/36633 | 11/1996 |
| WO | 97/00612 | 1/1997 |
| WO | 98/05652 | 2/1998 |

(Continued)

OTHER PUBLICATIONS

Berge et al, "Pharmaceutical Salts", Journal of Pharmaceutical Sciences, Jan. 1977, vol. 66, No. 1, pp. 1-19.

(Continued)

*Primary Examiner* — Deepak Rao
(74) *Attorney, Agent, or Firm* — Nixon & Vanderhye P.C.

(57) ABSTRACT

Compounds of formula (I):

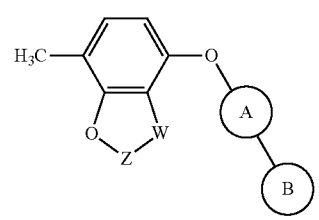

are described herein. Compounds of the disclosure are modulators of Kv3 channels and may be used in the prophylaxis or treatment of related disorders.

1 Claim, 3 Drawing Sheets

(56) References Cited

FOREIGN PATENT DOCUMENTS

| WO | 98/23155 | 6/1998 |
|---|---|---|
| WO | 98/23156 | 6/1998 |
| WO | 98/33382 | 8/1998 |
| WO | 01/076582 | 10/2001 |
| WO | 03/048134 | 6/2003 |
| WO | 03/066050 | 8/2003 |
| WO | 04/099159 | 11/2004 |
| WO | 2005/000309 | 1/2005 |
| WO | 2005/049580 | 6/2005 |
| WO | 2006/071471 | 7/2006 |
| WO | 2006/124118 | 11/2006 |
| WO | 2007/126765 | 11/2007 |
| WO | 2007/127010 | 11/2007 |
| WO | 2010/072598 | 7/2010 |
| WO | WO 2010/072598 | 7/2010 |
| WO | 2011/069951 | 6/2011 |
| WO | 2011/073114 | 6/2011 |
| WO | WO 2011/069951 | 6/2011 |
| WO | WO 2011/073114 | 6/2011 |
| WO | 2012/076877 | 6/2012 |
| WO | WO 2012/076877 | 6/2012 |
| WO | 2012/168710 | 12/2012 |

OTHER PUBLICATIONS

Harte et al, "Efficacy and relevance of the modulation of Ky3 channels to alleviate cognitive dysfunction in an animal model of schizaphrenia symptomatology", 4th Biennial Schizophrenia International Research Conference (Apr. 2014), Abstract.

Mabrouk et al, "A novel Kv3 positive modulator augments gamma frequency oscillations in the mammalian neocortex in vitro", $4^{th}$ Biennial Schizophrenia International Research Conference (Apr. 2014), Abstract.

Leger et al, "Two novel KV3 ion channel modulators alleviate cognitive dysfunction and social behaviour deficits of relevance to schizophrenia in an animal model", $4^{th}$ Biennial Schizophrenia International Research Conference (Apr. 2014), Abstract.

Neill et al, "A novel Kv3 ion channel modulator restores cognitive function in an animal model of cognitive impairment in schizophrenia", European College of Neuropsychopharmacology Conference (Oct. 2013), Abstract.

Sidor et al, "Potential anti-manic efficacy of a Kv3 channel modulator in a model of amphetamine-induced hyperactivity and in CLOCKΔ19 mutant mice", Society for Neuroscience Annual Meeting (Oct. 2012), Abstract.

Rudy and McBain, Kv3 channels: voltage-gated $K^+$ channels designed for high-frequency repetitive firing, Trends in Neurosciences, 24, 517-526, 2001.

Weiser et al., Differential Expression of Shaw-related $K^+$ Channels in the Rat Central Nervous System, J.Neurosci., 14, pp. 949-972, 1994.

Chow et al., J.Neurosci., $K^+$ Channel Expression Distinguishes Subpopulations of Parvalbumin-and Somatostatin-Containing Neocortical Interneurons, 19, pp. 9332-9345, 1999.

Martina et al., Functional and Molecular Differences between Voltage-Gated $K^+$ Channels of Fast-spiking Interneurons and Pyramidal Neurons of Rat Hippocampus, J.Neurosci., 18, pp. 8111-8125, 1998.

McDonald and Mascagni, Differential Expression of Kv3.1b and Kv3.2 Potassium Channel Subunits in Interneurons of the Basolateral Amygdala, J.Neurosci., 138, pp. 537-547, 2006.

International Search Report and Written Opinion for PCT/EP2010/068946, dated Mar. 18, 2011, Applicant: Glaxo Group Limited, Authorized officer: Roberto Menchaca.

International Search Report and Written Opinion for PCT/GB2011/052414, dated Feb. 24, 2012, Applicant: Autifony Therapeutics Limited, Authorized officer: Marc Gettins.

International Search Report and Written Opinion for PCT/GB2012/053045, dated Jan. 25, 2013, Applicant: Autifony Therapeutics Limited, Authorized officer: Marc Gettins.

International Search Report and Written Opinion for PCT/GB2012/051278, dated Jul. 13, 2012, Applicant: Autifony Therapeutics Limited, Authorized officer: Peter Bosma.

Chang et al., Distribution of Kv3.3 Potassium Channel Subunits in Distinct Neuronal Populations of Mouse Brain, J. Comp. Neurol., 502, pp. 953-972, 2007.

Kasten et al., Differential regulation of action potential firing in adult murine thalamocortical neurons by Kv3.2, Kv1 and SK potassium and N-type calcium channels, J.Physiol., 584, pp. 565-582, 2007.

Sacco et al., Properties and expression of Kv3 channels is cerebellar Purkinje cells, Mol. Cell. Neurosci., 33, pp. 170-179, 2006.

Li et al., Localization of Two High-Threshold Potassium Channel Subunits in the Rat Auditory System, J. Comp. Neurol., 437, pp. 196-218, 2001.

Joho et al., Increased γ- and Decreased σ-Oscillations in a Mouse Deficient for a Potassium Channel Expressed in Fast-Spiking Interneurons, J.Neurophysiol., 82, pp. 1855-1864, 1999.

Lau et al., Impaired Fast-Spiking, Suppressed Cortical Inhibition, and Increased Susceptibility to Seizures in Mice Lacking Kv3.2 $K^+$ Channel Proteins, J.Neurosci., 20, pp. 9071-9085, 2000.

McMahon et al., Allele-dependent changes of olivocerebellar circuit properties in the absence of the voltage-gated potassium channels Kv3.1 and Kv3.3, Eur. J.Neurosci., 19, pp. 3317-3327, 2004.

Espinosa et al., Alcohol Hypersensitivity, Increased Locomotion, and Spontaneous Myoclonus in Mice Lacking the Potassium Channels Kv3.1 and Kv3.3, J.Neurosci., 21, pp. 6657-6665, 2001.

Espinosa et al., Ablation of Kv3.1 and Kv3.3 Potassium Channels Disrupts Thalamocortical Oscillations In Vitro and In Vivo, J.Neurosci., 28, pp. 5570-5581, 2008.

Diochot et al., Sea Anemone Peptides with a Specific Blocking Activity against the Fast Inactivating Potassium Channel Kv3.4, J. Biol. Chem., 273, pp. 6744-6749, 1998.

Yeung et al., Modulation of Kv3 Subfamily Potassium Currents by the Sea Anemone Toxin BDS: Significance for CNS and Biophysical Studies, J.Neurosci., 25, pp. 8735-8745, 2005.

Atzori et al., $H_2$ histamine receptor-phosphorylation of Kv3.2 modulates interneuron fast spiking, Nat. Neurosci., 3, pp. 791-798, 2000.

Song et al., Acoustic environment determines phosphorylation state of the Kv3.1 potassium channel in auditory neurons, Nat Neurosci., 8, pp. 1335-1342, 2005.

Reynolds et al., Calcium Binding Protein Markers of GABA Deficits in Schizophrenia—Post Mortem Studies and Animal Models, Neurotox. Res., 6, pp. 57-61, 2004.

Benes et al., Circuitry based gene expression profiles in GABA cells of the trisynaptic pathway in schizophrenics versus bipolars, PNAS, 105, pp. 20935-20940, 2008.

Brambilla et al., GABAergic dysfunction in mood disorders, Mol. Psychiatry, 8, pp. 721-737, 2003.

Aroniadou-Anderjaska et al., Mechanisms regulating GABAergic inhibitory transmission in the basolateral amygdala: implications for epilepsy and anxiety disorders, Amino Acids, 32, pp. 305-315, 2007.

Ben-Ari, Seizures Beget Seizures: The Quest for GABA as a Key Player, Crit. Rev. Neurobiol., 18, pp. 135-144, 2006.

Markram et al., Interneurons of the Neocortical Inhibitory System, Nat.Rev.Neurosci., 5, pp. 793-807, 2004.

Fisahn, Kainate receptors and rhythmic activity in neuronal networks: hippocampal gamma oscillations as a tool, J.Physiol, 562, pp. 65-72, 2005.

Engel et al., Dynamic Predictions: Oscillations and Synchrony in Top-Down Processing, Nat.Rev.Neurosci., 2, pp. 704-716, 2001.

Spencer et al., Neural synchrony indexes disordered perception and cognition in schizophrenia, PNAS, 101, pp. 17288-17293, 2004.

Schulz and Steimer, Neurobiology of Circadian Systems, CNS Drugs, 23 Suppl 2, pp. 3-13, 2009.

Goldman and Holme, Hearing loss and tinnitus—the hidden healthcare time bomb, Drug Discovery Today, 15, pp. 253-255, 2010.

B. Shield, Evaluation of the social and economic costs of hearing impairment, a report for Hear-It AISBL: www.hear-it.org/multimedia/Hear_It_Report_October_2006.pdf, 2006.

(56) References Cited

OTHER PUBLICATIONS von Hehn et al., Loss of Kv3.1 Tonotopicity and Alterations in cAMP Response Element-Binding Protein Signaling in Central Auditory Neurons of Hearing Impaired Mice, J. Neurosci., 24, pp. 1936-1940, 2004.
Jung et al., Age-related changes in the distribution of Kv1.1 and Kv3.1 in rat cochlear nuclei, Neurol. Res., 27, pp. 436-440, 2005.
Kaczmarek et al., Regulation of the timing of MNTB neurons by short-term and long-term modulation of potassium channels, Hearing Res., 206, pp. 133-145, 2005.
Strumbos et al., Specific and Rapid Effects of Acoustic Stimulation on the Tonotopic Distribution of Kv3.1b Potassium Channels in the Adult Rat, J. Neuroscience, 167, pp. 567-572, 2010.
Strumbos et al., Fragile X Mental Retardation Protein Is Required for Rapid Experience-Dependent Regulation of Potassium Channel Kv3.1b, J. Neuroscience, 167, pp. 10263-10271, 2010.
Pilati et al., Acoustic over-exposure triggers burst firing in dorsal cochlear nucleus fusiform cells, Hearing Research, 283, pp. 98-106, 2012.
Waters et al. Mutations in voltage-gated potassium channel KCNC3 cause degenerative and developmental central nervous system phenotypes, Nature Genetics, 28, pp. 447-451, 2006.
Minassian et al. Altered Kc3.3 channel gating in early-onset spinocerebellar ataxia type 13, J. Physiol., 590.7, pp. 1599-1614, 2012.
International Search Report for PCT/GB2012/053045, dated Jan. 25, 2013, Gettins, Marc.
Written Opinion of the International Searching Authority for PCT/GB2012/053045, dated Jan. 25, 2013, Gettins, Marc.
Hans et al, "Tinnitus: Characteristics, Causes, Mechanisms, and Treatments", J Clin Neurol, 5, pp. 11-19 (2009).
Terracciano et al, "Fragile X syndrome", American Journal of Medial Genetics Part C (Seminars in Medical Genetics) 137C, pp. 32-37 (2005).
Rueda et al, "Systematic review of pharmacological treatments in fragile X syndrome", BMC Neurology, 9:53, pp. 1-11 (2009).
Pratt et al, "Modelling prefrontal cortex deficits in schizophrenia: implications for treatment", British Journal of Pharmacology, 153, pp. S465-S470 (2008).
McLennan et al, "Fragile X Syndrome", Current Genomics, 12 pp. 216-224 (2011).
Barry et al, "Activation of conventional kinesin motors in clusters by Shaw voltage-gated K+ channels", Journal of Cell Science, 126(9), pp. 2027-2041 (2013).
Tinnitus, American Academy of Otolaryngology—Head and Neck Surgery, http://www.entnet.org/content/tinnitus (2010).

\* cited by examiner hKv3.2 currents recorded using the assay described in Biological Example 1, at two concentrations of the compound of Reference Example RE1 hKv3.2 currents recorded using the assay described in Biological Example 1, at two concentrations of the compound of Reference Example RE3

COMPOUNDS

This application is a continuation application of U.S. application Ser. No. 14/816,476 (U.S. Patent Application Publication No. 2015-0336936 A1), filed Aug. 3, 2015 (issued as U.S. Pat. No. 9,422,272), which is a divisional application of U.S. application Ser. No. 14/361,510 (U.S. Patent Application Publication No. 2014-0323508 A1), filed May 29, 2014 (issued as U.S. Pat. No. 9,133,175), which is a U.S. national phase of International Application No. PCT/GB2012/053045), filed 6 Dec. 2012, which designated the U.S. and claims priority to GB Application No. PCT/GB2011/052414, filed 6 Dec. 2011, the entire contents of each of which are hereby incorporated by reference.

TECHNICAL FIELD

This invention relates to novel compounds, pharmaceutical compositions containing them and their use in therapy, in particular in the prophylaxis or treatment of hearing disorders, including hearing loss and tinnitus, as well as schizophrenia, bipolar disorder, epilepsy and sleep disorders.

BACKGROUND TO THE INVENTION

The Kv3 voltage-gated potassium channel family includes four members, Kv3.1, Kv3.2, Kv3.3, and Kv3.4. Genes for each of these subtypes can generate multiple isoforms by alternative splicing, producing versions with different C-terminal domains. Thirteen isoforms have been identified in mammals to date, but the currents expressed by these variants appear similar (Rudy and McBain, 2001, Trends in Neurosciences 24, 517-526). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy and McBain, 2001, Trends in Neurosci. 24, 517-526). Kv3.1-3 subtypes are predominant in the CNS, whereas Kv3.4 channels are found predominantly in skeletal muscle and sympathetic neurons (Weiser et al., 1994, J. Neurosci. 14, 949-972). Kv3.1-3 channel subtypes are differentially expressed by sub-classes of interneurons in cortical and hippocampal brain areas (e.g. Chow et al., 1999, J. Neurosci. 19, 9332-9345; Martina et al., 1998, J. Neurosci. 18, 8111-8125; McDonald and Mascagni, 2006, Neurosci. 138, 537-547, Chang et al., 2007, J. Comp. Neurol. 502, 953-972), in the thalamus (e.g. Kasten et al., 2007, J. Physiol. 584, 565-582), cerebellum (e.g. Sacco et al., 2006, Mol. Cell. Neurosci. 33, 170-179), and auditory brain stem nuclei (Li et al., 2001, J. Comp. Neurol. 437, 196-218).

Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999, J. Neurophysiol. 82, 1855-1864). The deletion of Kv3.2 leads to a reduction in seizure threshold and altered cortical electroencephalographic activity (Lau et al., 2000, J. Neurosci. 20, 9071-9085). Deletion of Kv3.3 is associated with mild ataxia and motor deficits (McMahon et al., 2004, Eur. J. Neurosci. 19, 3317-3327). Furthermore, reduction of function mutations of Kv3.3 channels in humans have been associated with spinocerebellar ataxia type 13 (Waters et al., 2006, Nat. Genet. 38, 447-451). Double deletion of Kv3.1 and Kv3.3 gives rise to a severe phenotype characterised by spontaneous seizures, ataxia, and an increased sensitivity to the effects of ethanol (Espinosa et al., 2001, J. Neurosci. 21, 6657-6665; Espinosa et al., 2008, J. Neurosci. 28, 5570-5581).

The known pharmacology of Kv3 channels is limited. Tetraethylammonium has been shown to inhibit the channels at low millimolar concentrations (Rudy and McBain, 2001, Trends in Neurosci. 24, 517-526), and blood-depressing substance (BDS) toxins from the sea anemone, *Anemonia sulcata* (Diochot et al., 1998, J. Biol. Chem. 273, 6744-6749), have been shown to selectively inhibit Kv3 channels with high affinity (Yeung et al., 2005, J. Neurosci. 25, 8735-8745). In addition to compounds acting directly on Kv3 channels, agonists of receptors that activate protein kinase A (PKA) and protein kinase C (PKC) have been shown to modulate Kv3-mediated currents in specific brain areas, leading to a reduction in the ability of the neurons to fire at high frequency (Atzori et al., 2000, Nat. Neurosci. 3, 791-798; Song et al., 2005, Nat Neurosci. 8, 1335-1342); these studies suggest that PKA and PKC can specifically phosphorylate Kv3 channels in a neuron-specific manner, causing a reduction in Kv3-mediated currents.

Bipolar disorder, schizophrenia, anxiety, and epilepsy are serious disorders of the central nervous system that have been associated with reduced function of inhibitory interneurons and gamma-amino butyric acid (GABA) transmission (Reynolds et al., 2004, Neurotox. Res. 6, 57-61; Benes et al., 2008, PNAS, 105, 20935-20940; Brambilla et al., 2003, Mol. Psychiatry. 8, 721-37, 715; Aroniadou-Anderjaska et al., 2007, Amino Acids 32, 305-315; Ben-Ari, 2006, Crit. Rev. Neurobiol. 18, 135-144). Parvalbumin positive basket cells that express Kv3 channels in the cortex and hippocampus play a key role in generating feedback inhibition within local circuits (Markram et al., 2004, Nat. Rev. Neurosci. 5, 793-807). Given the relative dominance of excitatory synaptic input over inhibitory input to glutamatergic pyramidal neurons in these circuits, fast-firing of interneurons supplying inhibitory input is essential to ensure balanced inhibition. Furthermore, accurate timing of inhibitory input is necessary to sustain network synchronisation, for example, in the generation of gamma frequency field potential oscillations that have been associated with cognitive function (Fisahn et al., 2005, J. Physiol 562, 65-72; Engel et al., 2001, Nat. Rev. Neurosci. 2, 704-716). Notably, a reduction in gamma oscillations has been observed in patients with schizophrenia (Spencer et al., 2004, PNAS 101, 17288-17293). Consequently, positive modulators of Kv3 channels might be expected to enhance the firing capabilities of specific groups of fast-firing neurons in the brain. These effects may be beneficial in disorders associated with abnormal activity of these neuronal groups.

In addition, Kv3.2 channels have been shown to be expressed by neurons of the superchiasmatic nucleus (SCN) the main circadian pacemaker in the CNS (Schulz and Steimer, 2009, CNS Drugs 23 Suppl 2, 3-13).

Hearing loss represents an epidemic that affects approximately 16% of the population in Europe and the US (Goldman and Holme, 2010, Drug Discovery Today 15, 253-255), with a prevalence estimated at 250 million people worldwide (B. Shield, 2006, Evaluation of the social and economic costs of hearing impairment. A report for Hear-It AISBL: www.hear-it.org/multimedia/Hear_It_Report_October_2006.pdf). As life expectancy continues to increase, so too will the number of people suffering from hearing disorders. Furthermore, it is believed that modern lifestyles may exacerbate this burden as the younger generation ages. Hearing conditions, including tinnitus have a profound effect on the quality of life, causing social isolation, depression, work and relationship difficulties, low self-esteem, and prejudice. Voltage-gated ion channels of the Kv3 family are expressed at high levels in auditory brainstem nuclei (Li et al., 2001, J. Comp. Neurol. 437, 196-218) where they permit the fast firing of neurons that transmit auditory information from the cochlear to higher brain regions. Loss of Kv3.1 channel expression in central auditory neurons is observed in hearing impaired mice (von Hehn et al., 2004, J. Neurosci. 24, 1936-1940), furthermore, a decline in Kv3.1 expression may be associated with loss of hearing in aged mice (Jung et al. 2005 Neurol. Res. 27, 436-440), and loss of Kv3 channel function may also follow noise-trauma induced hearing loss (Pilati et al., Hear Res. 2012 January 283(1-2):98-106). Furthermore, pathological plasticity of auditory brainstem networks is likely to contribute to symptoms that are experienced by many people suffering from hearing loss of different types. Recent studies have shown that regulation of Kv3.1 channel function and expression has a major role in controlling auditory neuron excitability (Kaczmarek et al., 2005, Hearing Res. 206, 133-145), suggesting that this mechanism could account for some of the plastic changes that give rise to tinnitus. These data support the hypothesis that positive modulation of Kv3 channels in auditory brainstem nuclei could have a therapeutic benefit in patients suffering from hearing loss. Finally, Fragile X syndrome and autism are frequently associated with hypersensitivity to sensory input, including auditory stimuli. Recent findings suggest that the protein coded by the FMR-I gene, whose mutation or absence gives rise to Fragile X syndrome, may directly regulate the expression of Kv3.1 channels in the auditory brainstem nuclei (Strumbos et al., 2010, J. Neuroscience, in press), suggesting that mis-regulation of Kv3.1 channels could give rise to hyperacusis in patients suffering from Fragile X or autism. Consequently, we propose that small molecule modulators of Kv3 channels in auditory brainstem nuclei could have a benefit in the treatment of disorders of hearing, including tinnitus and auditory hyper-acuity associated with Fragile X syndrome and autism.

Spinocerebellar ataxia type 13 (SCA13) is a human autosomal dominant disease caused by mutations in the KCNC3 gene that encodes the Kv3.3 channel. These mutations have been shown to cause a reduction in function of the channels (Waters et al., 2006, Nat. Genet. 38, 447-451; Minassian et al., 2012, J Physiol. 590.7, 1599-1614). Coexpression of Kv3.1 and Kv3.3 in many brain areas, including the cerebellum suggests some redundancy or the ability of one subtype to compensate for the absence of the other, indeed the phenotype of the Kv3.1/Kv3.3 double knockout mice is markedly more severe than either of the two single knockouts (e.g. Espinosa et al., 2008, J. Neurosci. 28, 5570-5581). Furthermore, it is possible that Kv3.1 and Kv3.3 proteins assemble to form heteromeric channels in some neurons. The ability of Kv3.1 to compensate for a loss of function of Kv3.3 may explain why certain mutations in the latter are only associated with an onset of spinocerebellar ataxia later in adult life, rather than from birth (Minassian et al., 2012, J Physiol. 590.7, 1599-1614). Consequently, small molecule modulators of either Kv3.3 or Kv3.1 might be beneficial in the treatment of spinocerebellar ataxia, in particular SCA13.

Patent applications WO2011/069951 and WO2012/076877 disclose compounds which are modulators of Kv3.1 and Kv3.2. Further, the value of such compounds is demonstrated in animal models of seizure, hyperactivity, sleep disorders, psychosis, cognitive deficit, bipolar disorder and hearing disorders.

There remains a need for the identification of alternative modulators of Kv3.1 and Kv3.2, in particular modulators of Kv3.1 and Kv3.2 which may demonstrate increased in vivo potency, certain channel selectivity profiles or desirable pharmacokinetic parameters that reduce the dose required for therapeutic effect in vivo. For certain therapeutic indications, there is also a need to identify compounds with a different modulatory effect on Kv3 channels, for example, compounds that alter the kinetics of channel gating or channel inactivation, and which may behave in vivo as negative modulators of the channels.

SUMMARY OF THE INVENTION

The present invention provides a compound of formula (I):

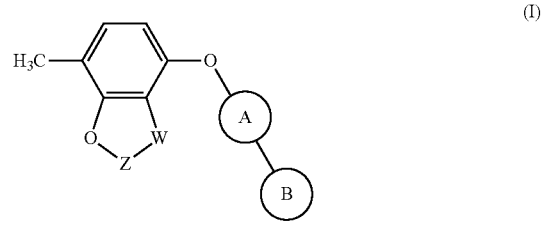

wherein:
W is $CR_aR_b$ or O;
  when W is $CR_aR_b$ then Z is $CH_2$;
  when W is O then Z is $CF_2$;
$R_a$ and $R_b$ are $CH_3$ or taken together form a $C_3$ spiro cycloalkyl;
  wherein, when W is $CR_aR_b$, Z is $CH_2$ and $R_a$ and $R_b$ are $CH_3$:
Ring A is:

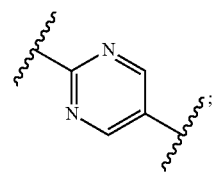

and Ring B is:

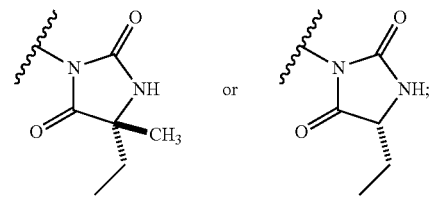

or
Ring A is:

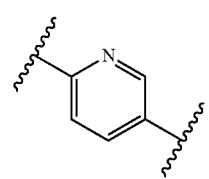 [SMILES: *c1ccc(*)nc1]

and Ring B is:

wherein, when W is $CR_aR_b$, Z is $CH_2$ and $R_a$ and $R_b$ taken together form a $C_3$ spiro cycloalkyl:
Ring A is:

or and
Ring B is:

or and
wherein, when W is O and Z is $CF_2$:
Ring A is:

and Ring B is:

A compound of formula (I) may be provided in the form of a pharmaceutically acceptable salt and/or solvate thereof.

In one embodiment of the invention a compound of formula (I) is provided in the form of a pharmaceutically acceptable salt.

The compounds of formula (I) may be used as medicaments, in particular for the prophylaxis or treatment of hearing disorders, including hearing loss and tinnitus, as well as schizophrenia, bipolar disorder, epilepsy and sleep disorders. The compounds of formula (I) may also be used as medicaments for the prophylaxis or treatment of cognition impairment or ataxia.

Further, there is provided a method for the prophylaxis or treatment of hearing disorders, including hearing loss and tinnitus, as well as schizophrenia, bipolar disorder, epilepsy and sleep disorders by administering to a subject a compound of formula (I). There is also provided a method for the prophylaxis or treatment of cognition impairment or ataxia by administering to a subject a compound of formula (I).

Compounds of formula (I) may be used in the manufacture of a medicament for the prophylaxis or treatment of hearing disorders, including hearing loss and tinnitus, as well as schizophrenia, bipolar disorder, epilepsy and sleep disorders. Compounds of formula (I) may also be used in the manufacture of a medicament for the prophylaxis or treatment of cognition impairment or ataxia.

Also provided are pharmaceutical compositions containing a compound of formula (I) and a pharmaceutically acceptable carrier or excipient.

DETAILED DESCRIPTION OF THE INVENTION

The present invention provides compounds of formula (I):

(I)

wherein:
W is $CR_aR_b$ or O;
when W is $CR_aR_b$ then Z is $CH_2$;
when W is O then Z is $CF_2$;
$R_a$ and $R_b$ are $CH_3$ or taken together form a $C_3$ spiro cycloalkyl;
wherein, when W is $CR_aR_b$, Z is $CH_2$ and $R_a$ and $R_b$ are $CH_3$:
Ring A is:

and Ring B is:

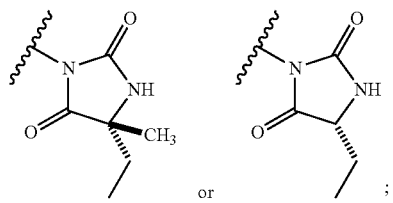

or

Ring A is:

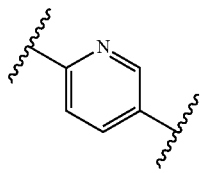 [SMILES: *c1ccc(*)nc1]

and Ring B is:

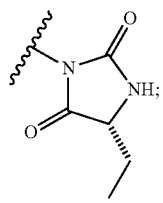

wherein, when W is CR$_a$R$_b$, Z is CH$_2$ and R$_a$ and R$_b$ taken together form a C$_3$ spiro cycloalkyl:

Ring A is:

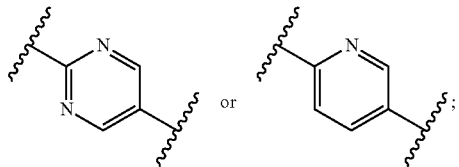 [SMILES: *c1cnc(*)nc1 ; *c1ccc(*)nc1]

and
Ring B is:

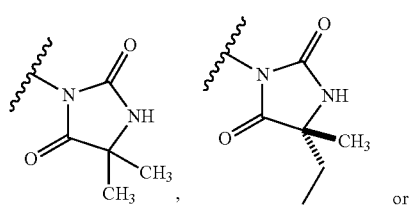

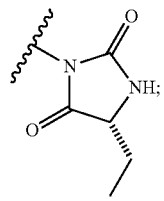

and
wherein, when W is O and Z is CF$_2$:
Ring A is:

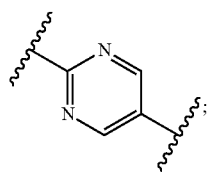 [SMILES: *c1cnc(*)nc1]

and Ring B is:

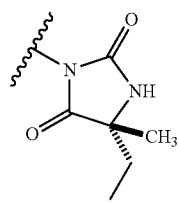 [SMILES: *N1C(=O)N[C@](C)(CC)C1=O]

or a pharmaceutically acceptable salt and/or solvate thereof.

Compounds of formula (I) may optionally be provided in the form of a pharmaceutically acceptable salt and/or solvate. In one embodiment of the invention a compound of formula (I) is provided in the form of a pharmaceutically acceptable salt. In a second embodiment of the invention a compound of formula (I) is provided in the form of a pharmaceutically acceptable solvate. In a third embodiment of the invention a compound of formula (I) is not in the form of a salt or solvate.

In another embodiment of the invention the compound is selected from the group consisting of:
(5R)-5-ethyl-5-methyl-3-[2-(7-methylspiro[2H-benzofuran-3,1'-cyclopropane]-4-yl)oxypyrimidin-5-yl]imidazolidine-2,4-dione;
(5R)-5-ethyl-5-methyl-3-{2-[(3,3,7-trimethyl-2,3-dihydro-1-benzofuran-4-yl)oxy]-5-pyrimidinyl}-2,4-imidazolidinedione;
(5R)-3-{2-[(2,2-difluoro-7-methyl-1,3-benzodioxol-4-yl)oxy]-5-pyrimidinyl}-5-ethyl-5-methyl-2,4-imidazolidinedione;
5,5-dimethyl-3-[2-(7-methylspiro[2H-benzofuran-3,1'-cyclopropane]-4-yl)oxypyrimidin-5-yl]imidazolidine-2,4-dione;
(5R)-5-ethyl-3-[2-(7-methylspiro[2H-benzofuran-3,1'-cyclopropane]-4-yl)oxypyrimidin-5-yl]imidazolidine-2,4-dione;
(5R)-5-ethyl-3-[6-(7-methylspiro[2H-benzofuran-3,1'-cyclopropane]-4-yl)oxy-3-pyridyl]imidazolidine-2,4-dione;
(5R)-5-ethyl-3-{6-[(3,3,7-trimethyl-2,3-dihydro-1-benzofuran-4-yl)oxy]-3-pyridinyl}-2,4-imidazolidinedione;

(5R)-5-ethyl-3-{2-[(3,3,7-trimethyl-2,3-dihydro-1-benzo-furan-4-yl)oxy]-5-pyrimidinyl}-2,4-imidazolidinedione;
(5R)-5-ethyl-5-methyl-3-[6-(7-methylspiro[2H-benzofuran-3,1'-cyclopropane]-4-yl)oxy-3-pyridyl]imidazolidine-2,4-dione;
5,5-dimethyl-3-[6-(7-methylspiro[2H-benzofuran-3,1'-cyclopropane]-4-yl)oxy-3-pyridyl]imidazolidine-2,4-dione; or a pharmaceutically acceptable salt thereof.

For the avoidance of doubt, the embodiments of any one feature of the compounds of the invention may be combined with any embodiment of another feature of compounds of the invention to create a further embodiment.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J. Pharm. Sci. (1977) 66, pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

Suitably, a pharmaceutically acceptable prodrug is formed by functionalising the secondary nitrogen of the hydantoin, for example with a group "L" as illustrated below (wherein R represents dimethyl, methyl and ethyl, or ethyl—see formula (I)):

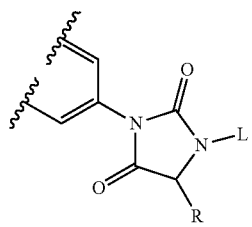

In one embodiment of the invention, a compound of formula (I) is functionalised via the secondary nitrogen of the hydantoin with a group L, wherein L is selected from:

a) —PO(OH)O$^-$.M$^+$, wherein M$^+$ is a pharmaceutically acceptable monovalent counterion,
b) —PO(O$^-$)$_2$.2M$^+$,
c) —PO(O$^-$)$_2$.D$^{2+}$, wherein D$^{2+}$ is a pharmaceutically acceptable divalent counterion,
d) —CH(R$^x$)—PO(OH)O$^-$.M$^+$, wherein R$^x$ is hydrogen or C$_{1-3}$ alkyl,
e) —CH(R$^x$)—PO(O$^-$)$_2$.2M$^+$,
f) —CH(R$^x$)—PO(O$^-$)$_2$.D$^{2+}$
g) —SO$_3^-$.M$^+$,
h) —CH(R$^x$)—SO$_3^-$.M$^+$, and
i) —CO—CH$_2$CH$_2$—CO$_2$.M$^+$.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The subject invention also includes isotopically-labelled compounds which are identical to those recited in formula (I) but for the fact that one or more atoms are replaced by an atom having an atomic mass or mass number different from the atomic mass or mass number most commonly found in nature. The skilled person will appreciate that in many circumstances the proportion of an atom having an atomic mass or mass number found less commonly in nature can also be been increased (referred to as "isotopic enrichment"). Examples of isotopes that can be incorporated into compounds of the invention include isotopes of hydrogen, carbon, nitrogen, oxygen, fluorine, iodine and chlorine such as $^3$H, $^{11}$C, $^{14}$C, $^{18}$F, $^{123}$I or $^{125}$I. Another isotope of interest is $^{13}$C. Another isotope of interest is $^2$H (deuterium).

Compounds of the present invention and pharmaceutically acceptable salts of said compounds that contain the aforementioned isotopes and/or other isotopes of other atoms are within the scope of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples and modifications thereof.

Compounds of formula (I), and salts and solvates thereof, may be prepared by the general methods outlined in WO2012/076877.

The present invention provides compounds of formula (I) or a pharmaceutically acceptable salt thereof for use in therapy.

The compounds of formula (I) or their pharmaceutically acceptable salts may be of use for the treatment or prophylaxis of a disease or disorder where a modulator of the Kv3.1 or Kv3.2 or Kv3.1 and Kv3.2 channels is required. As used herein, a modulator of Kv3.1 or Kv3.2 or Kv 3.1 and Kv3.2 is a compound which alters the properties of these channels, either positively or negatively.

Compounds of the invention may be tested in the assay of Biological Example 1 to determine their modulatory properties.

In certain disorders it may be of benefit to utilise a modulator of Kv3.1 or Kv3.2 which demonstrates a particular selectivity profile between the two channels. For example a compound may be selective for modulation of Kv3.1 channels over modulation of Kv3.2 channels demonstrating, for example, at least a 2 fold, 5 fold or 10 fold activity for Kv3.1 channels than for Kv3.2 channels. Alternatively, a compound may be selective for modulation of Kv3.2 channels over modulation of Kv3.1 channels demonstrating, for example, at least a 2 fold, 5 fold or 10 fold activity for Kv3.2 channels than for Kv3.1 channels. In other cases a compound may demonstrate comparable activity between modulation of Kv3.1 and Kv3.2 channels, for example the activity for each channel is less than 2 fold that for the other channel, such as less than 1.5 fold or less than 1.2 fold. The activity of a compound is suitably quantified by its potency as indicated by an EC50 value.

Diseases or conditions that may be mediated by modulation of Kv3.1 and/or Kv3.2 channels may be selected from the list below. The numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10).

The compounds of formula (I) or their pharmaceutically acceptable salts may be of use for the treatment or prophylaxis of depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90); Seasonal affective disorder.

The compounds of formula (I) or their pharmaceutically acceptable salts may be of use for the treatment or prophylaxis of schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The compounds of formula (I) or their pharmaceutically acceptable salts may be of use for the treatment or prophylaxis of anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

The compounds of formula (I) or their pharmaceutically acceptable salts may be of use for the treatment or prophylaxis of substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-Induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative-, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

The compounds of formula (I) or their pharmaceutically acceptable salts may be of use for the enhancement of cognition including the treatment of cognition impairment in other diseases such as schizophrenia, bipolar disorder, depression, other psychiatric disorders and psychotic conditions associated with cognitive impairment, e.g. Alzheimer's disease. Alternatively, the compounds of formula (I) or their pharmaceutically acceptable salts and/or solvates may be of use for the prophylaxis of cognition impairment, such as may be associated with diseases such as schizophrenia, bipolar disorder, depression, other psychiatric disorders and psychotic conditions associated with cognitive impairment, e.g. Alzheimer's disease.

The compounds of formula (I) or their pharmaceutically acceptable salts may be of use for the treatment or prophylaxis of sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The compounds of formula (I) or their pharmaceutically acceptable salts may be of use for the treatment or prophylaxis of eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

The compounds of formula (I) or their pharmaceutically acceptable salts may be of use for the treatment or prophylaxis of Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

The compounds of formula (I) or their pharmaceutically acceptable salts may be of use for the treatment or prophylaxis of Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

The compounds of formula (I) or their pharmaceutically acceptable salts may be of use for the treatment or prophylaxis of Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

The compounds of formula (I) or their pharmaceutically acceptable salts may be of use for the treatment or prophylaxis of Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of formula (I) or their pharmaceutically acceptable salts may be of use for the treatment or prophylaxis of Impulse control disorder including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

The compounds of formula (I) or their pharmaceutically acceptable salts may be of use for the treatment or prophylaxis of hearing disorders including auditory neuropathy, auditory processing disorder, hearing loss, which includes sudden hearing loss, noise induced hearing loss, substance-induced hearing loss, and hearing loss in adults over 60 (presbycusis), and tinnitus.

The compounds of formula (I) or their pharmaceutically acceptable salts may be of use for the treatment or prophylaxis of Ménière's disease, disorders of balance, and disorders of the inner ear.

The compounds of formula (I) or their pharmaceutically acceptable salts may be of use for the treatment or prophylaxis of hyperacusis and disturbances of loudness perception, including Fragile-X syndrome and autism.

The compounds of formula (I) or their pharmaceutically acceptable salts may be of use for the treatment or prophylaxis of Epilepsy, (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, partial and generalised seizures (including tonic, clonic, tonic-clonic, atonic, myoclonic, absence seizures), secondarily generalized seizures, temporal lobe epilepsy, absence epilepsies (including childhood, juvenile, myoclonic, photo- and pattern-induced), severe epileptic encephalopathies (including hypoxia-related and Rasmussen's syndrome), febrile convulsions, epilepsy partialis continua, progressive myoclonus epilepsies (including Unverricht-Lundborg disease and Lafora's disease), post-traumatic seizures/epilepsy including those related to head injury, simple reflex epilepsies (including photosensitive, somatosensory and proprioceptive, audiogenic and vestibular), metabolic disorders commonly associated with epilepsy such as pyridoxine-dependent epilepsy, Menkes' kinky hair disease, Krabbe's disease, epilepsy due to alcohol and drug abuse (e.g. cocaine), cortical malformations associated with epilepsy (e.g. double cortex syndrome or subcortical band heterotopia), chromosomal anomolies associated with seizures or epilepsy such as Partial monosomy (15Q)/Angelman syndrome.

In one embodiment of the invention, there is provided a compound of formula (I) or a pharmaceutically acceptable salt thereof for the treatment or prophylaxis of depression and mood disorders, hearing disorders, schizophrenia, substance abuse disorders, sleep disorders or epilepsy.

In one embodiment of the invention, there is provided a compound of formula (I) or a pharmaceutically acceptable salt thereof for the treatment or prophylaxis of bipolar disorder or mania.

In one embodiment of the invention, there is provided a compound of formula (I) or a pharmaceutically acceptable salt and/or solvate thereof for the treatment or prophylaxis of ataxia, such as spinocerebellar ataxia.

In one embodiment of the invention, there is provided a compound of formula (I) or a pharmaceutically acceptable salt and/or solvate thereof for the treatment or prophylaxis of cognition impairment.

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

The invention also provides a method of treating or preventing a disease or disorder where a modulator of Kv3 is required, for example those diseases and disorders mentioned hereinabove, which comprises administering to a subject in need thereof an effective amount of a compound of formula (I) or a pharmaceutically acceptable salt thereof.

The invention also provides a compound of formula (I), or a pharmaceutically acceptable salt thereof, for use in the treatment or prophylaxis of a disease or disorder where a modulator of Kv3 is required, for example those diseases and disorders mentioned hereinabove.

The invention also provides the use of a compound of formula (I), or a pharmaceutically acceptable salt thereof, in the manufacture of a medicament for the treatment or prophylaxis of a disease or disorder where a modulator of Kv3 is required, for example those diseases and disorders mentioned hereinabove.

The invention also provides a method of treating depression and mood disorders, schizophrenia, substance abuse disorders, sleep disorders or epilepsy, for example for those indications mentioned hereinabove, which comprises administering to a subject in need thereof an effective amount of a Kv3 modulator or a pharmaceutically acceptable salt thereof.

For use in therapy the compounds of the invention are usually administered as a pharmaceutical composition. The invention also provides a pharmaceutical composition comprising a compound of formula (I), or a pharmaceutically acceptable salt thereof, and a pharmaceutically acceptable carrier.

The compounds of formula (I) or their pharmaceutically acceptable salts may be administered by any convenient method, e.g. by oral, parenteral, buccal, sublingual, nasal, rectal or transdermal administration, and the pharmaceutical compositions adapted accordingly. Other possible routes of administration include intratympanic and intracochlear.

The compounds of formula (I) or their pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable derivative thereof together with a further therapeutic agent or agents.

The invention provides a compound of formula (I), for use in combination with a further therapeutic agent or agents.

When the compounds are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Furthermore, the invention relates to a method for manufacturing compounds of formula (I), to novel intermediates of use in the manufacture of compounds of formula (I) and to the manufacture of such intermediates.

Particular intermediates of interest include:
7-methylspiro[2H-benzofuran-3,1'-cyclopropane]-4-ol (Intermediate 13)

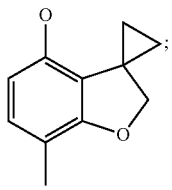

and
3,3,7-trimethyl-2,3-dihydro-1-benzofuran-4-ol (Intermediate 27)

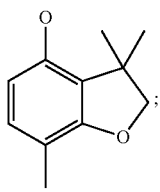

and
2,2-difluoro-7-methyl-1,3-benzodioxol-4-ol (Intermediate 37)

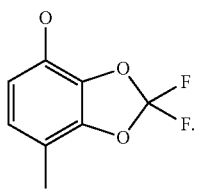

Other intermediates of interest are the anilides:
6-(7-methylspiro[2H-benzofuran-3,1'-cyclopropane]-4-yl)oxypyridin-3-amine (Intermediate 15)

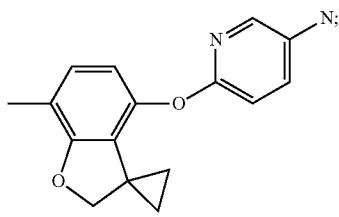

and
2-(7-methylspiro[2H-benzofuran-3,1'-cyclopropane]-4-yl)oxypyrimidin-5-amine (Intermediate 19)

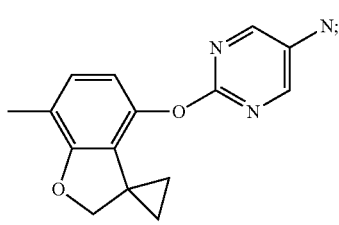

and

6-[(3,3,7-trimethyl-2,3-dihydro-1-benzofuran-4-yl)oxy]-3-pyridinamine (Intermediate 29)

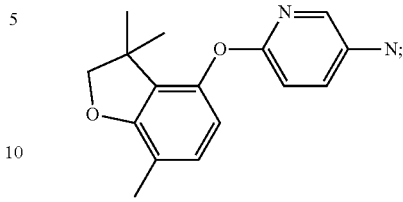

and
2-[(3,3,7-trimethyl-2,3-dihydro-1-benzofuran-4-yl)oxy]-5-pyrimidinamine (Intermediate 33)

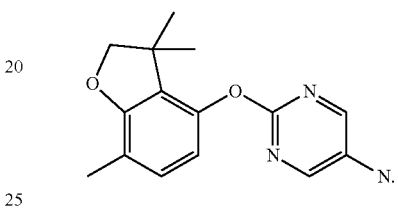

All publications, including but not limited to patents and patent applications, cited in this specification are herein incorporated by reference as if each individual publication were specifically and individually indicated to be incorporated by reference herein as though fully set forth.

BRIEF DESCRIPTION OF THE DRAWINGS

The present invention is illustrated, by way of example only, with reference to the following figures in which.

EXPERIMENTAL

Figure 1A:
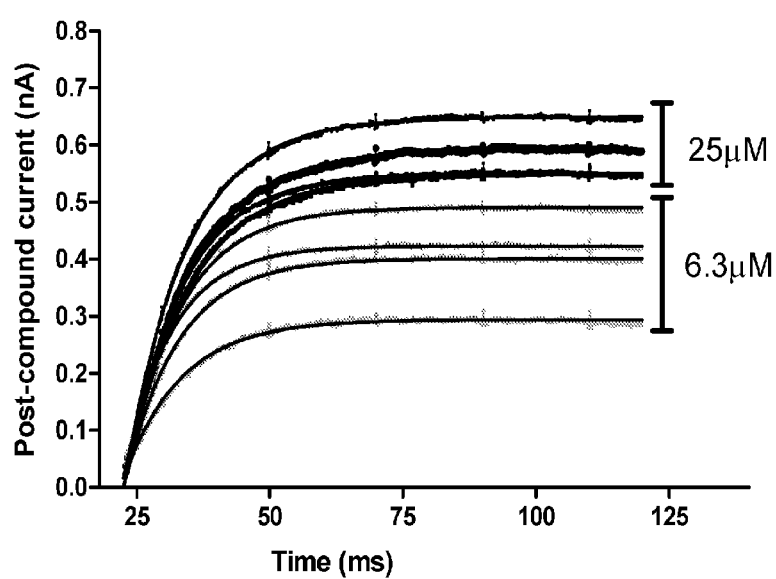
FIG. 1A hKv3.2 currents recorded using the assay described in Biological Example 1. Data shown are the individual currents over the period of the depolarising voltage step to −15 mV recorded from 4 different cells at two concentrations of the compound of Reference Example RE1. The data are fitted by a single exponential curve (solid lines) using the fitting procedure in Prism version 5 (Graphpad Software Inc).

The invention is illustrated by the compounds described below. The following examples describe the laboratory synthesis of specific compounds of the invention and are not meant to limit the scope of the invention in any way with respect to compounds or processes. It is understood that, although specific reagents, solvents, temperatures and time periods are used, there are many possible equivalent alternatives that can be used to produce similar results. This invention is meant to include such equivalents.

Analytical Equipment

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities ranging from for example 85% to 98%. Calculations of number of moles and yield are in some cases adjusted for this.

Nuclear Magnetic Resonance (NMR) spectra ($^1$H; $^{13}$C and $^{19}$F) were recorded either on Varian instruments at 300, 400, 500 or 600 MHz, or on Bruker instruments at 400 MHz. Chemical shifts are reported in ppm (δ) using the residual solvent line as internal standard. Splitting patterns are designed as s (singlet), br.s (broad singlet), d (doublet), t (triplet), q (quartet), dd (doublet of doublets), dt (doublet of triplets) and m (multiplet). The NMR spectra were recorded at temperatures ranging from 25 to 30° C.

Direct infusion Mass spectra (MS) were run on a mass spectrometer, operating in ES (+) and ES (−) ionization mode coupled with an HPLC instrument Agilent 1100 Series [LC/MS-ESI(+) analyses were performed on a Supelcosil ABZ+Plus (33×4.6 mm, 3 μm) (mobile phase: from 10% [CH$_3$CN+0.05% TFA] to 90%[CH$_3$CN+0.05% TFA] and 10% [water] in 2.2 min, under these conditions for 2.8 min. T=45° C., flux=0.9 mL/min)]. The use of this methodology is indicated by "MS_2 (ESI)" in the analytic characterization of the described compounds.

Quality Control:

LC/MS-ES+ under acidic conditions was performed on a Zorbax SB C18 column (1.8 μm 3×50 mm). Mobile phase: A: (H2O+0.05% TFA by vol.)/B: (CH$_3$CN+0.05% TFA by vol). Gradient: t=0 min 0% (B), from 0 to 95% (B) in 2.5 min, 95% (B) for 0.2 min, from 95 to 100% (B) in 0.2 min, 100% (B) for 0.4 min, From 100% to 0% (B) in 0.1 min. Stop time 4 min. Column T=60° C. Flow rate: 1.5 ml/min. Mass range ES+: (100-1000 amu, F=60). UV detection wavelengths: DAD 1A=220.8, DAD 1B=254.8. The use of this methodology is indicated by "LC/MS: QC_3_MIN" in the analytic characterization of the described compounds.

Ultra Performance Liquid Chromatography with an Acidic Gradient:

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ mass spectrometer operating in positive or negative electrospray ionisation mode [LC/MS-ES (+ or −): analyses were performed using an Acquity™ UPLC BEH C18 column (50×2.1 mm, 1.7 μm particle size). General Method: Mobile phase: A: (water+0.1% HCO2H)/B: (CH3CN+0.06% HCO2H). Gradient: t=0 min 3% (B), t=0.05 min 6% (B), t=0.57 min 70% (B), t=1.06 min 99% (B) lasting for 0.389 min, t=1.45 min 3% (B), stop time 1.5 min. Column T=40° C. Flow rate=1.0 mL/min. Mass range: ES (+): 100-1000 amu. ES (−): 100-800 amu. UV detection range: 210-350 nm. The use of this methodology is indicated by "UPLC" in the analytic characterization of the described compounds.

Ultra Performance Liquid Chromatography with a Basic Gradient:

Total ion current (TIC) and DAD UV chromatographic traces together with MS and UV spectra associated with the peaks were taken on a UPLC/MS Acquity™ system equipped with PDA detector and coupled to a Waters SQD mass spectrometer operating in positive and negative alternate electrospray ionisation mode [LC/MS-ES+/−: analyses were performed using an Acquity™ UPLC BEH C18 column (50×2.1 mm, 1.7 μm particle size). Mobile phase: A: (10 mM aqueous solution of NH4HCO3 (adjusted to pH 10 with ammonia))/B: CH3CN. Gradient: t=0 min 3% (B), t=1.06 min 99% (B) lasting for 0.39 min, t=1.46 min 3% (B), stop time 1.5 min. Column T=40° C. Flow rate=1.0 mL/min. Mass range: ES (+): 100-1000 amu. ES (−): 100-1000 amu. UV detection range: 220-350 nm. The use of this methodology is indicated by "UPLC_B" in the analytic characterization of the described compounds.

In a number of preparations, purification was performed using Biotage automatic flash chromatography (SP1 and SP4) or Flash Master Personal systems.

Flash chromatographies were carried out on silica gel 230-400 mesh (supplied by Merck AG Darmstadt, Germany) or on silica gel 300-400 mesh (supplied by Sinopharm Chemical Reagent Co., Ltd.), Varian Mega Be—Si pre-packed cartridges, pre-packed Biotage silica cartridges (e.g. Biotage SNAP cartridge).

ABBREVIATIONS

AIBN azobisisobutyronitrile
BuLi butyllithium
CDCl$_3$ deutrated chloroform
CCl$_4$ carbon tetrachloride
D$_2$O deutrated water
DCM dichloromethane
DIAD Diisopropyl azodicarboxylate
DIPEA N,N-diisopropylethylamine
DMAP 4-dimethylaminopyridine
DMF N,N-dimethylformamide
DMSO dimethylsulfoxide
DMSO-d$_6$ deutrated dimethylsulfoxide
Et$_2$O diethyl ether
EtOAc ethyl acetate
EtOH ethanol
h hours
H$_2$O$_2$ Hydrogen peroxide
HATU (O-7-azabenzotriazol-1-yl)-N,N,N',N'-tetramethyluroniumhexafluorophosphate)
HCO2H formic acid
HCl hydrogen chloride
K$_2$CO$_3$ potassium carbonate
KHMDS potassium hexamethyldisilazide
KOH potassium hydroxide
LiAlH$_4$ Lithium aluminum hydride
MeCN/CH$_3$CN acetonitrile
MeOH methanol
MDAP mass-directed autopurification
MOM methoxymethyl
MOM-Cl chloromethyl methyl ether
NaH sodium hydride
Na$_2$SO$_4$ sodium sulphate
NBS N-Bromosuccinimide
Na$_2$CO$_3$ sodium carbonate
NaOH sodium hydroxide
NaOMe sodium methoxide
NH4OH ammonium hydroxide NH4HCO3H ammonium bicarbonate
NMR Nuclear Magnetic Resonance
Pd/C palladium on charcoal
PE petroleum ether
r.t. room temperature
sec-BuLi sec-Butyllithium
SCRC Sinopharm Chemical Reagent Co., Ltd
T3P propylphosphonic anhydride
TBAF Tetrabutylammonium fluoride
TBME Methyl tert-butyl ether
TEA triethylamine
TFA trifluoroacetic acid
THF tetrahydrofuran Intermediate 1

1-(methyloxy)-3-{[(methyloxy)methyl]oxy}benzene

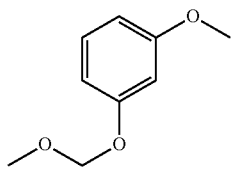

To a solution of 3-(methyloxy)phenol (10.38 g, 84 mmol) in tetrahydrofurane (100 ml, SCRC) was added NaH (60% wt., 1.824 g, 76 mmol, Aldrich) portionwise under ice-cooling. The reaction mixture was stirred at room temperature for 1 hour and bromomethyl methyl ether (9.5 g, 76 mmol, SCRC) was then added. The resulting mixture was stirred at room temperature for 2 hours and water (50 ml) was added. The reaction mixture was extracted with ethyl acetate (2 times 50 ml, SCRC) and the combined organic layers were dried over sodium sulphate, evaporated. The residue was purified by column chromatography on silica gel (EtOAc:PE=1:100) to afford the title compound (10.2 g) as a colorless liquid.

Intermediate 2

2-iodo-1-(methyloxy)-3-{[(methyloxy)methyl]oxy}benzene

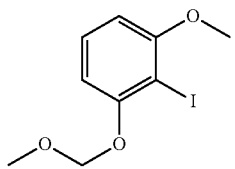

To a solution of 1-(methyloxy)-3-{[(methyloxy)methyl]oxy}benzene (Intermediate 1, 10 g, 59.5 mmol) in tetrahydrofurane (100 ml, SCRC) precooled to −78° C. was added dropwise BuLi (2.5 M in THF, 28.5 ml, 71.3 mmol, SCRC), maintaining the inner temperature lower than −70° C. After the addition was complete, the mixture was stirred at −70° C. for 2 hours and a solution of iodine (15.09 g, 59.5 mmol, SCRC) in THF (50 ml, SCRC) was added dropwise. The resulting mixture was stirred for 2 hours at room temperature and quenched with a saturated aqueous solution of ammonium chloride (100 ml). The mixture was extracted with ethyl acetate (3 times 300 ml, SCRC) and the combined organic layers were dried, evaporated and purified by silica gel chromatography with as eluents EtOAc:PE (1/100) to afford the title compound (16.2 g) as a yellow liquid.

Intermediate 3

2-iodo-3-(methyloxy)phenol

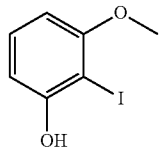

To a solution of 2-iodo-1-(methyloxy)-3-{[(methyloxy)methyl]oxy}benzene (Intermediate 2, 16.2 g, 55.1 mmol) in dichloromethane (100 ml, SCRC) was bubbled HCl (g) for 30 mins. TLC showed that the reaction was completed. The reaction mixture was poured into an aqueous saturated solution of NaHCO$_3$ (200 ml) and extracted with dichloromethane (3×200 ml, SCRC). The combined organic layers were dried, evaporated and purified by column chromatography on silica gel (EtOAc:PE=1:50) to afford the title compound as a yellow liquid (10.3 g).

Intermediate 4

2-iodo-1-(methyloxy)-3-[(2-methyl-2-propen-1-yl)oxy]benzene

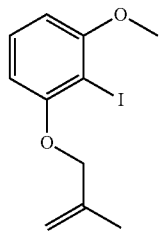

To a solution of 2-iodo-3-(methyloxy)phenol (Intermediate 3, 10.3 g) in DMF (100 ml, SCRC) was added NaH (60%, wt., 1.977 g, 49.4 mmol) portionwise. The reaction mixture was stirred at room temperature for 1 hour and 3-chloro-2-methyl-1-propene (3.73 g, 41.2 mmol, Aldrich) was added. The resulting mixture was stirred at room temperature for 2 hours and water (50 ml) was added. The reaction mixture was extracted with ethyl acetate (3 times 200 ml, SCRC) and the combined organic layer were dried, evaporated and purified by silica gel chromatography with as eluents EtOAc/PE (1/30) to afford the title compound as a yellow liquid (11.6 g)

$^1$H-NMR (400 MHz, CDCl$_3$) δ ppm: 7.25 (1H, t), 6.52-6.47 (2H, m), 5.21 (1H, s), 5.01 (1H, s), 4.49 (2H, s), 3.89 (3H, s), 1.87 (3H, s)

Intermediate 5

3,3-dimethyl-4-(methyloxy)-2,3-dihydro-1-benzofuran

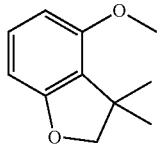

To a solution of 2-iodo-1-(methyloxy)-3-[(2-methyl-2-propen-1-yl)oxy]benzene (Intermediate 4, 6.08 g) in toluene (50 ml, SCRC) were added AIBN (3.61 g, 21.99 mmol, SCRC) and tributylstannane (11.60 g, 40.0 mmol, Aldrich). The reaction mixture was heated at reflux for 3 hours and then cooled to room temperature. Water (100 ml) was added and the mixture was extracted with ethyl acetate (3 times 200 ml, SCRC). The combined organic layers were dried, evaporated and purified by silica gel chromatography with as eluents EtOAc/PE (1/50) to afford the title compound as a yellow liquid (2.7 g).

$^1$H-NMR (400 MHz, DMSO-$d_6$) δ ppm: 7.05 (1H, t), 6.50 (1H, d), 6.39 (1H, d), 4.14 (2H, s), 3.77 (3H, s), 1.34 (6H, s);

Intermediate 6

3,3-dimethyl-2,3-dihydro-1-benzofuran-4-ol

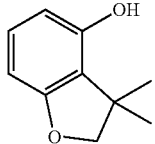

To a solution of 3,3-dimethyl-4-(methyloxy)-2,3-dihydro-1-benzofuran (Intermediate 5, 4.0 g) in dichloromethane (100 ml, SCRC) was added BBr3 (6.37 ml, 67.3 mmol, SCRC) dropwise under ice-cooling. After the addition was complete, the reaction mixture was stirred for 2 hours at room temperature and then water (20 ml) was added. The resulting mixture was extracted with ethyl acetate (3 times 100 ml, SCRC) and the combined organic layers were dried, evaporated and purified by silica gel chromatography with EtOAc/PE as eluents (1/20) to afford the title compound (2.8 g).

$^1$H-NMR (400 MHz, CDCl$_3$) δ ppm: 6.98-6.94 (1H, t), 6.41-6.39 (1H, dd), 6.25-6.23 (1H, dd), 4.21 (2H, s), 1.45 (6H, s); MS_2: 163 [M−H]−.

Intermediate 7

2,4-bis(methoxymethoxy)-1-methyl-benzene

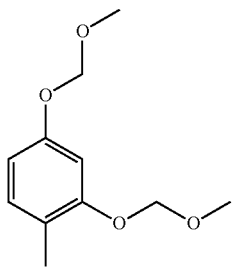

To a solution of 4-methylbenzene-1,3-diol (4 g, 32.26 mmol) in dry N,N-Dimethylformamide (30 ml) at 0° C. sodium hydride (60% dispersion in mineral oil) (3.87 g, 96.78 mmol) was added and the reaction mixture was stirred for 15 minutes at the same temperature. MOM-Cl (7.35 ml, 96.78 mmol) was quickly added and the reaction mixture was stirred for 1 hour while the temperature was allowed to reach room temperature. The reaction was quenched with brine (40 ml) and extracted with ethyl acetate (3×80 ml). The organic layer was washed with ice cold brine (2×50 ml), dried over sodium sulphate, filtered and evaporated and the residue was purified by flash chromatography (Biotage system) on silica gel using a 100 g SNAP column and cyclohexane to cyclohexane/ethyl acetate 8:2 as eluents affording the title compound (6.1 g) as a colourless oil.

LC/MS: QC_3_MIN: Rt=1.811 min; 213 [M+H]+.

Intermediate 8 ethyl 2-[2,6-bis(methoxymethoxy)-3-methyl-phenyl]-2-oxo-acetate

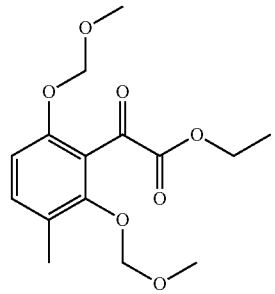 [SMILES: CCOC(=O)C(=O)c1c(OCOC)ccc(C)c1OCOC]

To a solution of 2,4-bis(methoxymethoxy)-1-methyl-benzene (Intermediate 7, 5.5 g, 25.94 mmol) in dry tetrahydrofuran (50 ml) at room temperature BuLi 1.6M in hexane (19.45 ml, 31.13 mmol) was added and the reaction mixture was stirred for 30 minutes at the same temperature. The mixture was cooled to −78° C. and it was added (via cannulation) to a solution of ethyl chlorooxoacetate (4.35 ml, 38.9 mmol) in dry tetrahydrofuran (30 ml) at −78° C. The reaction mixture was stirred at −78° C. for 30 minutes. The reaction was quenched with water (20 ml), diluted with brine (50 ml) and extracted with ethyl acetate (2×100 ml). Combined organic layers were dried over sodium sulphate, filtered and evaporated. The residue was purified by flash chromatography (Biotage system) on silica gel using a 100 g SNAP column and cyclohexane to cyclohexane/ethyl acetate 8:2 as eluent affording the title compound (4.65 g) as a light yellow oil.

LC/MS: QC_3_MIN: Rt=1.865 min.

Intermediate 9 ethyl 2-[2,6-bis(methoxymethoxy)-3-methyl-phenyl] prop-2-enoate

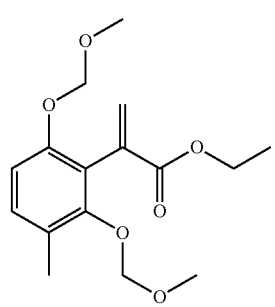 [SMILES: C=C(C(=O)OCC)c1c(OCOC)ccc(C)c1OCOC]

To a suspension of methyltriphenylphosphonium bromide (8.78 g, 24.6 mmol) in dry tetrahydrofuran (50 ml) at 0° C. KHMDS 0.5M solution in toluene (44.22 ml, 22.11 mmol) was slowly added and the reaction mixture was stirred for 15 minutes at 0° C. and for 45 minutes at room temperature. The reaction mixture was cooled to 0° C. and it was slowly added to a solution of ethyl 2-[2,6-bis(methoxymethoxy)-3-methyl-phenyl]-2-oxo-acetate (Intermediate 8, 4.6 g, 14.74 mmol) in dry tetrahydrofuran (25 mL) at 0° C. and the reaction mixture was stirred for 2 hours at 0° C. The reaction was quenched with water (50 ml), diluted with brine (50 ml) and extracted with ethyl acetate (2×100 ml). The organic layer was dried over sodium sulphate, filtered and evaporated. The residue was purified by flash chromatography (Biotage system) on silica gel using a 100 g SNAP column and cyclohexane to cyclohexane/ethyl acetate 8:2 as eluents affording the title compound (3.8 g) as a colourless oil.

LC/MS: QC_3_MIN: Rt=1.930 min.

Intermediate 10 ethyl 1-[2,6-bis(methoxymethoxy)-3-methyl-phenyl] cyclopropanecarboxylate

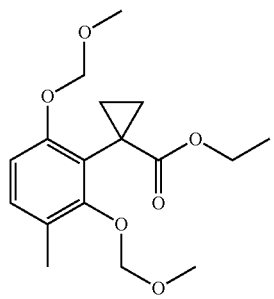 [SMILES: CCOC(=O)C1(c2c(OCOC)ccc(C)c2OCOC)CC1]

To a solution of trimethylsulfoxonium iodide (4.4 g, 20 mmol) in dry dimethyl sulfoxide (30 mL) sodium hydride (60% dispersion in mineral oil) (0.720 g, 18 mmol) was added and the reaction mixture was stirred for 1 hour at room temperature. A solution of ethyl 2-[2,6-bis (methoxymethoxy)-3-methyl-phenyl]prop-2-enoate (Intermediate 9, 3.5 g, 11.29 mmol) in dry dimethyl sulfoxide (15 mL) was slowly added and the reaction mixture was stirred for 1 hour at room temperature. The reaction was quenched with an aqueous saturated solution of ammonium chloride (10 ml), diluted with water (40 ml) and extracted with ethyl acetate (2×100 ml). The organic layer was washed with water (2×50 ml), dried over sodium sulphate, filtered and evaporated. The residue was purified by flash chromatography (Biotage system) on silica gel using a 100 g SNAP column and cyclohexane to cyclohexane/ethyl acetate 8:2 as eluents affording the title compound (3.1 g) as a colourless oil.

LC/MS: QC_3_MIN: Rt=2.028 min.

Intermediate 11

2-[1-(hydroxymethyl)cyclopropyl]-3-(methoxymethoxy)-6-methyl-phenol

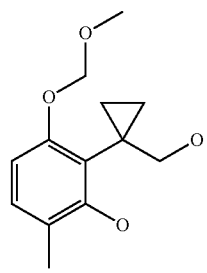 [SMILES: COCOc1ccc(C)c(O)c1C1(CO)CC1]

To a solution of ethyl 1-[2,6-bis(methoxymethoxy)-3-methyl-phenyl]cyclopropanecarboxylate (Intermediate 10, 300 mg, 0.93 mmol) in ethanol (10 ml) HCl 6N in water (0.4 mL, 2.4 mmol) was added and the reaction mixture was stirred overnight at 50° C. Combined solvents were removed under reduced pressure. The residue was suspended in dry toluene (10 mL) and the solvent evaporated. The obtained residue was dissolved in dry tetrahydrofuran (10 ml), the mixture was cooled to 0° C. and NaH (60% dispersion in mineral oil) (80 mg, 2 mmol) was added and the reaction mixture was stirred for 30 minutes at the same temperature. MOM-Cl (0.083 mL, 1.1 mmol) was then added and the reaction mixture was stirred for 1 hour at 0° C. LiAlH$_4$ (1M in THF, 1.2 ml, 1.2 mmol) was added and the reaction mixture was further stirred for 1 hour at the same temperature. The reaction was quenched with an aqueous saturated solution of ammonium chloride (10 ml), diluted with water (20 ml) and extracted with ethyl acetate (2×50 ml). Combined organic layers were dried over sodium sulphate, filtered and evaporated and the residue was purified by flash chromatography (Biotage system) on silica gel using a 25 g SNAP column and cyclohexane to cyclohexane/ethyl acetate 7:3 as eluents affording the title compound (70 mg) as a white solid.

LC/MS: QC_3_MIN: Rt=1.690 min; 239 [M+H]+.

Intermediate 12

4-(methoxymethoxy)-7-methyl-spiro[2H-benzo-furan-3,1'-cyclopropane]

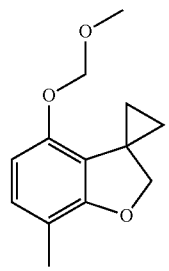 [SMILES: COCOc1ccc(C)c2c1C1(CC1)CO2]

To a solution of 2-[1-(hydroxymethyl)cyclopropyl]-3-(methoxymethoxy)-6-methyl-phenol (Intermediate 11, 65 mg, 0.27 mmol) in dry tetrahydrofuran (5 ml) triphenylphosphine (84 mg, 0.32 mmol) was added and the reaction mixture was stirred until complete dissolution of it. DIAD (0.056 ml, 0.285 mmol) was then added dropwise and the reaction mixture was stirred for 30 minutes at room temperature. The solvent was removed under reduced pressure and the residue was purified by flash chromatography (Biotage system) on silica gel using a 10 g SNAP column and cyclohexane to cyclohexane/ethyl acetate 8:2 as eluents affording the title compound (40 mg) as a light yellow oil.

LC/MS: QC_3_MIN: Rt=2.024 min; 221 [M+H]+.

Intermediate 13

7-methylspiro[2H-benzofuran-3,1'-cyclopropane]-4-ol

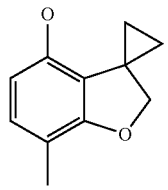

To a solution of 4-(methoxymethoxy)-7-methyl-spiro[2H-benzofuran-3,1'-cyclopropane] (Intermediate 12, 38 mg, 0.17 mmol) in ethanol (5 ml), HCl 6N in water (0.1 mL, 0.6 mmol) was added and the reaction mixture was stirred for 4 days at room temperature. Combined solvents were removed under reduced pressure and the residue was purified by flash chromatography (Biotage system) on silica gel using a 10 g SNAP column and cyclohexane to cyclohexane/ethyl acetate 7:3 as eluents affording the title compound (24 mg) as a light orange solid.

$^1$H-NMR (400 MHz, DMSO-$d_6$) δ ppm: 9.02 (1H, s), 6.65 (1H, d), 6.06 (1H, d), 4.36 (2H, s), 2.02 (3H, s), 1.40-1.44 (2H, m), 0.77-0.82 (2H, m). ROESY (400 MHz, DMSO-$d_6$): NOE correlation between proton at 6.65 ppm and protons (CH3) at 2.02 ppm, NOE correlation between proton at 9.02 ppm and proton at 6.06 ppm. LC/MS: QC 3 MIN: Rt=1.647 min; 177 [M+H]+.

Intermediate 14

2-(7-methylspiro[2H-benzofuran-3,1'-cyclopropane]-4-yl)oxy-5-nitro-pyridine

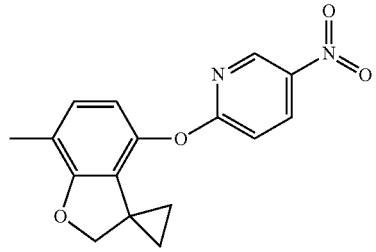 [SMILES: Cc1ccc(Oc2ccc([N+](=O)[O-])cn2)c2c1OCC21CC1]

To a solution of 7-methylspiro[2H-benzofuran-3,1'-cyclopropane]-4-ol (Intermediate 13, 176 mg, 1 mmol) in dry DMF (4 ml) potassium carbonate (207 mg, 1.5 mmol) and then 2-chloro-5-nitropyridine (158 mg, 1 mmol) were added and the reaction mixture was stirred for 2 hours at 80° C. After cooling the reaction mixture was quenched with water (2 ml), diluted with brine (10 ml) and extracted with ethyl acetate (2×20 ml). The organic layer was dried over sodium sulfate, filtered and evaporated affording the title compound (270 mg) as an orange solid that was used in the next step as crude material without further purification.

LC/MS: QC 3 MIN: Rt=2.138 min; 299 [M+H]+.

Intermediate 15

6-(7-methylspiro[2H-benzofuran-3,1'-cyclopropane]-4-yl)oxypyridin-3-amine

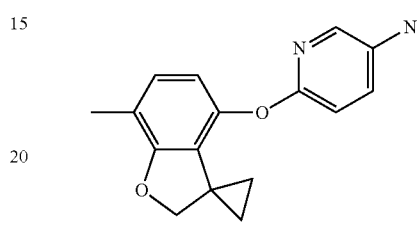

To a solution of 2-(7-methylspiro[2H-benzofuran-3,1'-cyclopropane]-4-yl)oxy-5-nitro-pyridine (Intermediate 14, 265 mg) in tetrahydrofuran (5 ml)/water (2.5 ml) iron (245 mg, 4.45 mmol) and then ammonium chloride (238 mg, 4.45 mmol) were added and the reaction mixture was stirred overnight at room temperature. The catalyst was filtered off and the residue was diluted with an aqueous saturated solution of NaHCO$_3$ (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 1:1 as eluents affording the title compound (203 mg) as a light yellow solid.

LC/MS: QC 3 MIN: Rt=1.740 min; 269 [M+H]+.

Intermediate 16 tert-butyl N-[(1R)-1-[[6-(7-methylspiro[2H-benzofuran-3,1'-cyclopropane]-4-yl)oxy-3-pyridyl]carbamoyl]propyl]carbamate

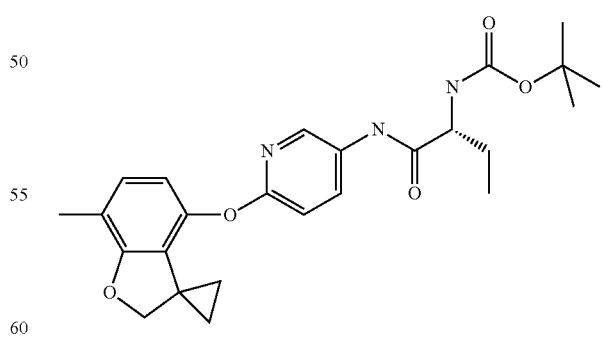

To a solution of (2R)-2-({[(1,1-dimethylethyl)oxy]carbonyl}amino)butanoic acid (36 mg, 0.18 mmol) in dry DMF (1 ml) DIPEA (52 µl, 0.3 mmol) and then HATU (65 mg, 0.17 mmol) were added and the reaction mixture was stirred for 15 minutes at r.t. 6-(7-methylspiro[2H-benzofuran-3,1'-cyclopropane]-4-yl)oxypyridin-3-amine (Intermediate 15, 40 mg, 0.15 mmol) was then added and the reaction mixture was stirred for 4 hours at room temperature. The reaction was quenched with water (2 ml) diluted with brine (5 ml) and extracted with ethyl acetate (2×10 ml). The organic layer was dried (Na₂SO₄), filtered and evaporated and the residue was purified by flash chromatography (Biotage system) on silica gel using a 10 g SNAP column and cyclohexane/ethyl acetate 90:10 to cyclohexane/ethyl acetate 60:40 as eluents affording the title compound (57 mg) as a white solid.

LC/MS: QC_3_MIN: Rt=2.190 min; 454 [M+H]+.

Intermediate 17

(2R)-2-amino-N-[6-(7-methylspiro[2H-benzofuran-3,1'-cyclopropane]-4-yl)oxy-3-pyridyl]butanamide

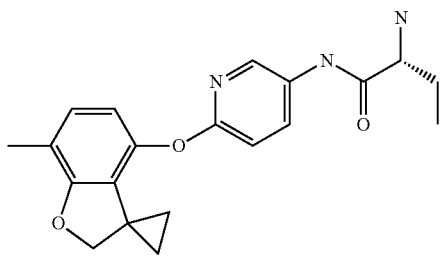 [SMILES: CC[C@@H](N)C(=O)Nc1ccc(Oc2ccc(C)c3c2C2(CC2)CO3)nc1]

To a solution of tert-butyl N-[(1R)-1-[[6-(7-methylspiro[2H-benzofuran-3,1'-cyclopropane]-4-yl)oxy-3-pyridyl]carbamoyl]propyl]carbamate (Intermediate 16, 55 mg) in dry DCM (3 ml) at 0° C. TFA (1 ml) was slowly added and the reaction mixture was stirred for 3 hours at the same temperature. The solvent and the excess of TFA were removed under reduced pressure and the residue was diluted with DCM (10 ml) and an aqueous saturated solution NaHCO₃ was added while the pH was allowed to reach ~8. Two phases were separated and the organic layer was dried (Na₂SO₄), filtered and evaporated affording the title compound (41 mg) as white solid.

LC/MS: QC_3_MIN: Rt=1.792 min; 354 [M+H]+.

Intermediate 18

2-(7-methylspiro[2H-benzofuran-3,1'-cyclopropane]-4-yl)oxy-5-nitro-pyrimidine

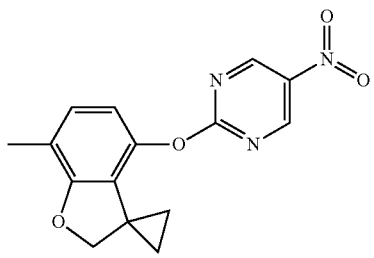 [SMILES: Cc1ccc(Oc2ncc([N+](=O)[O-])cn2)c2c1OCC21CC1]

To a solution of 7-methylspiro[2H-benzofuran-3,1'-cyclopropane]-4-ol (Intermediate 13, 176 mg, 1 mmol) in dry Acetonitrile (4 ml) potassium carbonate (207 mg, 1.5 mmol) and then 2-chloro-5-nitropyrimidine (159 mg, 1 mmol) were added and the reaction mixture was stirred for 24 hours at 80° C. After cooling the reaction mixture was quenched with water (2 ml), diluted with brine (10 ml) and extracted with ethyl acetate (2×20 ml). The organic layer was dried over sodium sulfate, filtered and evaporated affording the title compound (258 mg) as an orange solid that was used in the next step as crude material without further purification.

LC/MS: QC 3 MIN: Rt=2.007 min; 300 [M+H]+.

Intermediate 19

2-(7-methylspiro[2H-benzofuran-3,1'-cyclopropane]-4-yl)oxypyrimidin-5-amine

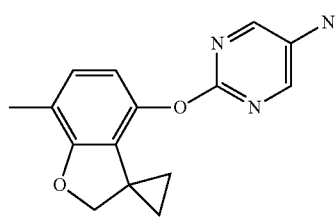 [SMILES: Cc1ccc(Oc2ncc(N)cn2)c2c1OCC21CC1]

To a solution of 2-(7-methylspiro[2H-benzofuran-3,1'-cyclopropane]-4-yl)oxy-5-nitro-pyrimidine (Intermediate 18, 255 mg) in tetrahydrofuran (5 ml)/water (2.5 ml) iron (234 mg, 4.25 mmol) and then ammonium chloride (227 mg, 4.25 mmol) were added and the reaction mixture was stirred for 48 hours at room temperature. The catalyst was filtered off and the residue was diluted with an aqueous saturated solution of NaHCO₃ (5 ml) and extracted with ethyl acetate (3×10 ml). The organic layer was dried over sodium sulphate, filtered and evaporated and the residue was purified by flash chromatography (Biotage system) on silica gel using a 10 g SNAP column and cyclohexane/ethyl acetate 8:2 to cyclohexane/ethyl acetate 4:6 as eluents affording the title compound (52 mg) as a light orange solid.

LC/MS: QC 3 MIN: Rt=1.746 min; 270 [M+H]+.

Intermediate 20 tert-butyl N-[(1R)-1-[[2-(7-methylspiro[2H-benzofuran-3,1'-cyclopropane]-4-yl)oxypyrimidin-5-yl]carbamoyl]propyl]carbamate

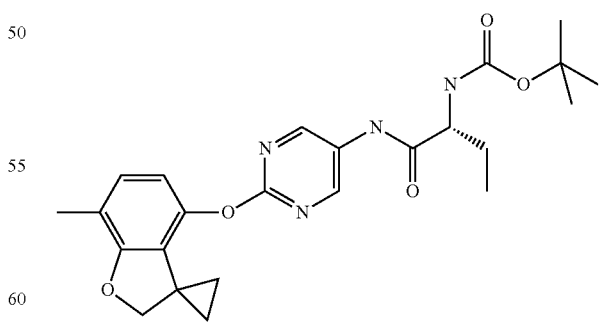

To a solution of (2R)-2-({[(1,1-dimethylethyl)oxy]carbonyl}amino)butanoic acid (45 mg, 0.222 mmol) in dry DMF (1 ml) DIPEA (87 µl, 0.5 mmol) and then HATU (80 mg, 0.21 mmol) were added and the reaction mixture was stirred for 15 minutes at r.t. 2-(7-methylspiro[2H-benzofuran-3,1'-cyclopropane]-4-yl)oxypyrimidin-5-amine (Intermediate 19, 50 mg, 0.185 mmol) was then added and the reaction mixture was stirred for 6 hours at room temperature. The reaction was quenched with water (2 ml) diluted with brine (5 ml) and extracted with ethyl acetate (2×10 ml). The organic layer was dried (Na$_2$SO$_4$), filtered and evaporated and the residue was purified by flash chromatography (Biotage system) on silica gel using a 10 g SNAP column and cyclohexane/ethyl acetate 90:10 to cyclohexane/ethyl acetate 60:40 as eluents affording the title compound (45 mg) as a white solid.

LC/MS: QC 3 MIN: Rt=2.109 min; 455 [M+H]+.

Intermediate 21

(2R)-2-amino-N-[2-(7-methylspiro[2H-benzofuran-3,1'-cyclopropane]-4-yl)oxypyrimidin-5-yl]butanamide

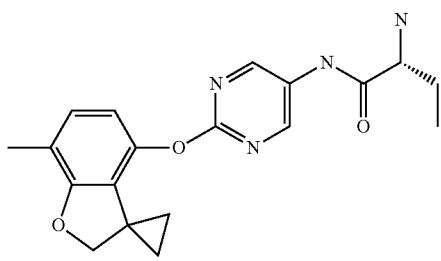 [SMILES: CC[C@@H](N)C(=O)Nc1cnc(Oc2ccc(C)c3c2C2(CC2)CO3)nc1]

To a solution of tert-butyl N-[(1R)-1-[[2-(7-methylspiro[2H-benzofuran-3,1'-cyclopropane]-4-yl)oxypyrimidin-5-yl]carbamoyl]propyl]carbamate (Intermediate 20, 42 mg) in dry DCM (3 ml) at 0° C. TFA (1 ml) was slowly added and the reaction mixture was stirred for 3 hours at the same temperature. The solvent and the excess of TFA were removed under reduced pressure and the residue was diluted with DCM (10 ml) and an aqueous saturated solution NaHCO$_3$ was added while the pH was allowed to reach ~8. Two phases were separated and the organic layer was dried (Na$_2$SO$_4$), filtered and evaporated affording the title compound (25 mg) as light yellow gum.

LC/MS: QC 3 MIN: Rt=1.688 min; 355 [M+H]+.

Intermediate 22

(5R)-3-(2-chloropyrimidin-5-yl)-5-ethyl-5-methyl-imidazolidine-2,4-dione

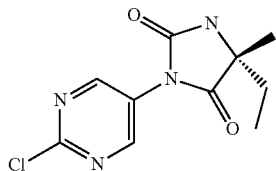 [SMILES: CC[C@@]1(C)NC(=O)N(c2cnc(Cl)nc2)C1=O]

To a solution of triphosgene (1.38 g, 4.65 mmol) in Ethyl acetate (20 ml) at 0° C. a solution of 2-chloro-5-aminopyrimidine (1 g, 7.75 mmol)/DIPEA (8 ml, 4.65 mmol) in ethyl acetate (40 ml) was slowly added (20 minutes) and the reaction mixture was stirred for 15 minutes at the same temperature. Maintaining the reaction mixture at 0° C., vacuum was applied (10 minutes) for removing the excess of phosgene. A solution of DMAP (0.945 g, 7.75 mmol) in ethyl acetate/dichloromethane 1:1 (8 ml) was added and the reaction mixture was stirred for 5 minutes at the same temperature. A solution of methyl (R)-2-amino-2-methyl-butyrate hydrochloride (2.59 g, 15.5 mmol) in ethyl acetate (30 ml) was slowly added (15 minutes) at 0° C. and the reaction mixture was stirred for 30 minutes at the same temperature. The reaction was quenched with aqueous buffer (pH3) while the pH was allowed to reach ~5-6 and two phases were separated. The organic layer was washed with aqueous buffer (pH3) (2×20 ml) and then brine (20 ml), dried (Na$_2$SO$_4$), filtered and evaporated affording the urea intermediate as orange foam. The urea was dissolved in MeOH (20 ml), NaOMe (0.41 g, 7.75 mmol) was added and the reaction mixture was stirred for 15 minutes at r.t. The mixture was quenched with an aqueous saturated solution of ammonium chloride (25 ml) and diluted with ethyl acetate (50 ml). Two phases were separated and the organic layer was washed with brine (2×20 ml), dried (Na$_2$SO$_4$), filtered and evaporated. The residue was triturated with Et$_2$O (10 ml) and the solid collected affording the title compound (1.22 g) as a beige solid.

LC/MS: QC 3 MIN: Rt=1.341 min; 255 [M+H]+.

Intermediate 23

3-(2-chloropyrimidin-5-yl)-5,5-dimethyl-imidazolidine-2,4-dione

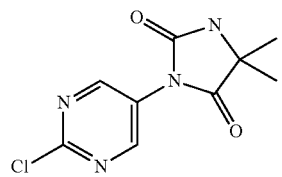 [SMILES: CC1(C)NC(=O)N(c2cnc(Cl)nc2)C1=O]

To a solution of triphosgene (1.38 g, 4.65 mmol) in Ethyl acetate (20 ml) at 0° C. a solution of 2-chloro-5-aminopyrimidine (1 g, 7.75 mmol)/DIPEA (8 ml, 4.65 mmol) in ethyl acetate (40 ml) was slowly added (20 minutes) and the reaction mixture was stirred for 15 minutes at the same temperature. Maintaining the reaction mixture at 0° C., vacuum was applied (10 minutes) for removing the excess of phosgene. A solution of DMAP (0.945 g, 7.75 mmol) in ethyl acetate/dichloromethane 1:1 (8 ml) was added and the reaction mixture was stirred for 5 minutes at the same temperature. 2,2-Dimethylglycine methyl ester hydrochloride (2.37 g, 15.5 mmol) in ethyl acetate (30 ml) was slowly added (15 minutes) at 0° C. and the reaction mixture was stirred for 30 minutes at the same temperature. The reaction was quenched with aqueous buffer (pH3) while the pH was allowed to reach ~5-6 and two phases were separated. The organic layer was washed with aqueous buffer (pH3) (2×20 ml) and then brine (20 ml), dried (Na$_2$SO$_4$), filtered and evaporated affording the urea intermediate as orange foam. The urea was dissolved in MeOH (20 ml), NaOMe (0.41 g, 7.75 mmol) was added and the reaction mixture was stirred for 15 minutes at r.t. The mixture was quenched with an aqueous saturated solution of ammonium chloride (25 ml) and diluted with ethyl acetate (50 ml). Two phases were separated and the organic layer was washed with brine (2×20 ml), dried (Na$_2$SO$_4$), filtered and evaporated. The residue was triturated with Et$_2$O (10 ml) and the solid collected affording the title compound (1.08 g) as an orange solid.

LC/MS: QC 3 MIN: Rt=1.062 min; 241 [M+H]+.

Intermediate 24

[(3,3-dimethyl-2,3-dihydro-1-benzofuran-4-yl)oxy][tris(1-methylethyl)]silane

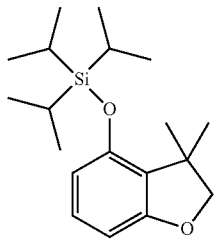 [SMILES: CC(C)[Si](Oc1cccc2c1C(C)(C)CO2)(C(C)C)C(C)C]

3,3-Dimethyl-2,3-dihydro-1-benzofuran-4-ol (Intermediate 6, 3.6 g, 21.91 mmol) was dissolved in anhydrous THF (20.0 mL) and the colorless solution was cooled to 0° C. stirring under nitrogen. A 2M n-BuLi solution in cyclohexane (13.2 mL, 26.4 mmol) was added drop wise and the resulting yellow solution was stirred at 0° C. for 10 min. Triisopropylsislyltriflate (7.7 mL, 28.5 mmol) was added drop wise: the solution discolored almost completely. This was allowed to warm to room temperature and stirred over night. Water (1.0 mL) was added to and volatiles evaporated under reduced pressure. The residue was dissolved in ethyl acetate and washed with brine three times. The organic layer was dried over anhydrous $Na_2SO_4$ and evaporated to dryness to give yellow oil which was re-dissolved in TBME and washed twice with water. The organic solution was dried over $Na_2SO_4$ and evaporated to dryness to give the title compound (7.4 g) as a yellow oil.

$^1$H NMR (400 MHz, DMSO-$d_6$) δ ppm 6.94 (1H, t), 6.31-6.36 (1H, m), 6.29 (1H, d), 4.14 (2H, s), 1.28-1.40 (9H, m), 1.09 (18H, d).

Intermediate 25

[(7-bromo-3,3-dimethyl-2,3-dihydro-1-benzofuran-4-yl)oxy][tris(1-methylethyl)]silane

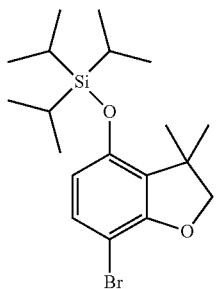 [SMILES: CC(C)[Si](Oc1ccc(Br)c2c1C(C)(C)CO2)(C(C)C)C(C)C]

[(3,3-dimethyl-2,3-dihydro-1-benzofuran-4-yl)oxy][tris(1-methylethyl)]silane (Intermediate 24, 7.4 g, 23.19 mmol) was dissolved in THF (70.0 mL). N-Bromosuccinimide (4.2 g, 23.88 mmol) was added dissolving in few minutes. This mixture was stirred at room temperature for 3 hrs. More NBS (0.64 g, 3.48 mmol) was added and the reaction mixture was stirred at room temperature for a further hour. $CCl_4$ (50 mL) was added to the reaction mixture and the solution was evaporated to dryness. The residue was re-suspended in $CCl_4$ and stirred at room temperature for 15 min. The white solid was removed by filtration and the wet cake was washed with more $CCl_4$. The $CCl_4$ was swapped with ethyl acetate and the organic solution was washed three times with 2.5% w/w aqueous $NaHCO_3$ and finally with water. The organic solution was dried on anhydrous $Na_2SO_4$ and evaporated to dryness to give the title compound (8.6 g) as a brown oil.

$^1$H NMR (400 MHz, DMSO-$d_6$) δ ppm 7.14 (1H, d), 6.29 (1H, d), 4.24 (2H, s), 1.27-1.41 (9H, m), 1.08 (18H, d).

Intermediate 26 tris(1-methylethyl)[(3,3,7-trimethyl-2,3-dihydro-1-benzofuran-4-yl)oxy]silane

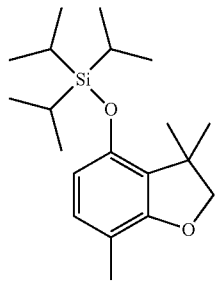 [SMILES: Cc1ccc(O[Si](C(C)C)(C(C)C)C(C)C)c2c1OCC2(C)C]

[(7-bromo-3,3-dimethyl-2,3-dihydro-1-benzofuran-4-yl)oxy][tris(1-methylethyl)]silane (Intermediate 25, 7.1 g, 17.72 mmol) was dissolved in anhydrous THF (72 mL) and cooled to 0° C. Tetramethylethylenediamine (8.0 mL, 53.16 mmol) was added and the yellow solution was stirred at 0° C. for 10 min. A solution of 1.6 M butyllithium in hexane (22.5 mL, 35.4 mmol) was added drop wise over 10 minutes and then stirred at 0° C. for 15 min. Methyl iodide (11 mL, 177.2 mmol) was added drop wise over 6 min. The white solid was removed by filtration and the wet cake was washed in with THF. The combined organic layers were evaporated to dryness. The residue was dissolved in ethyl acetate and washed twice with aqueous $NaHCO_3$ and once with water. The organic solution was dried on anhydrous $Na_2SO_4$ and evaporated to dryness. to give brown oil. The residue was purified by flash chromatography on silica gel using cyclohexane to cyclohexane/ethyl acetate 1:1 as eluents affording the title compound (3.6 g) as a brown oil.

$^1$H NMR (400 MHz, DMSO-$d_6$) δ ppm 6.76 (1H, d), 6.20 (1H, d), 4.14 (2H, s), 2.02 (3H, s), 1.28-1.39 (9H, m), 1.09 (18H, d).

Intermediate 27

3,3,7-trimethyl-2,3-dihydro-1-benzofuran-4-ol

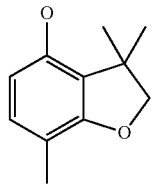

Tris(1-methylethyl)[(3,3,7-trimethyl-2,3-dihydro-1-benzofuran-4-yl)oxy]silane (Intermediate 26, 3.6 g, 10.84 mmol) was dissolved in THF (36 mL) to obtain a dark yellow solution. TBAF (8.5 g, 32.5 mmol) was added and the reaction mixture was stirred overnight at room temperature. The solvent was removed under reduced pressure. The residue was dissolved in ethyl acetate and washed with aqueous HCl, then aqueous $NaHCO_3$ and finally brine. The organic solution was dried over Na₂SO₄ and evaporated to dryness and the residue was purified by flash chromatography on silica gel using cyclohexaneto cyclohexane/ethyl acetate 95:5 as eluents affording the title compound (1.69 g) as colorless oil.

¹H NMR (400 MHz, DMSO-d₆) δ ppm 9.06 (1H, s), 6.65-6.69 (1H, m), 6.19 (1H, d), 4.11 (2H, s), 1.99 (3H, s), 1.33 (6H, s).

Intermediate 28

5-nitro-2-[(3,3,7-trimethyl-2,3-dihydro-1-benzofuran-4-yl)oxy]pyridine

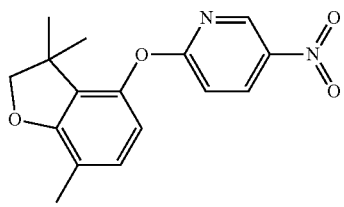 [SMILES: Cc1ccc(Oc2ccc([N+](=O)[O-])cn2)c2c1OCC2(C)C]

3,3,7-trimethyl-2,3-dihydro-1-benzofuran-4-ol (Intermediate 27, 0.9 g, 5.0 mmol) was dissolved in CH₃CN (5 mL) in the presence of 2-chloro-5-nitropyridine (790 mg, 5.0 mmol) and K₂CO₃ (1.72 g, 12.5 mmol) and the resulting suspension was heated to 60° C. for 1.5 hrs. The mixture was then cooled to room temperature and diluted with water and ethyl acetate. Two phases were separated and the organic layer was washed with brine, then dried over Na₂SO₄ and evaporated to dryness, The residue was purified by flash chromatography on silica gel using cyclohexaneto cyclohexane/ethyl acetate 90:10 as eluents affording the title compound (0.92 g) as yellowish solid.

¹H-NMR (400 MHz, DMSO-d₆): δ ppm 9.04 (1H, d), 8.61 (1H, dd), 7.24 (1H, d), 7.02 (1H, d), 6.54 (1H, d), 4.21 (2H, s), 2.14 (3H, s), 1.21 (6H, s). ¹³C-NMR (200 MHz, DMSO-d₆): δ ppm 166.6, 158.7, 147.2, 144.8, 140.4, 135.8, 130.2, 126.1, 116.7, 114.5, 111.0, 83.6, 42.2, 26.0, 14.4.

Intermediate 29

6-[(3,3,7-trimethyl-2,3-dihydro-1-benzofuran-4-yl)oxy]-3-pyridinamine

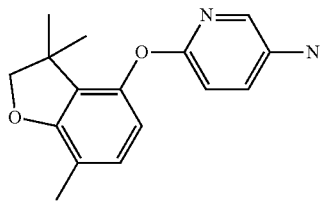 [SMILES: Cc1ccc(Oc2ccc(N)cn2)c2c1OCC2(C)C]

5-Nitro-2-[(3,3,7-trimethyl-2,3-dihydro-1-benzofuran-4-yl)oxy]pyridine (Intermediate 28, 920 mg, 3.0 mmol) was dissolved in EtOH (13.5 mL) and stirred under hydrogen atmosphere (2 bar) in the presence of Pd/C 10% w/w (46 mg, 5% w/w) at room temperature for 30 minutes. The catalyst was filtered off, washed with THF and the resulting solution evaporated to dryness to afford an orange solid. The crude product was crystallized from MeOH to the title compound (565 mg) as a beige solid.

¹H-NMR (400 MHz, DMSO-d₆): δ ppm 7.51 (1H, d), 7.05 (1H, dd), 6.85 (1H, d), 6.69 (1H, d), 6.21 (1H, d), 5.04 (2H, br.s), 4.19 (2H, s), 2.08 (3H, s), 1.30 (6H, s). ¹³C-NMR (200 MHz, DMSO-d₆): δ ppm 158.3, 154.2, 150.7, 141.5, 132.2, 129.6, 125.3, 124.7, 113.9, 112.2, 111.8, 83.7, 42.2, 26.0, 14.4.

Intermediate 30

1,1-dimethylethyl {(1R)-1-[({6-[(3,3,7-trimethyl-2,3-dihydro-1-benzofuran-4-yl)oxy]-3-pyridinyl}amino)carbonyl]propyl}carbamate

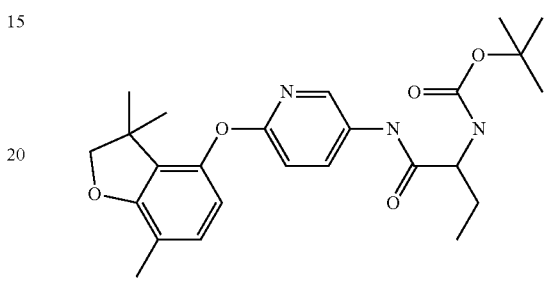

6-{[3,3,7-Trimethyl-6-(trifluoromethoxy)-2,3-dihydro-1-benzofuran-4-yl]oxy}pyridin-3-amine (Intermediate 29, 405 mg, 1.27 mmol) was suspended in ethyl acetate (4 mL). Triethylamine (0.44 ml, 3.175 mmol) was added followed by the addition of (2R)-2-({[(1,1-dimethylethyl)oxy]carbonyl}amino)butanoic acid (258 mg, 1.27 mmol). The resulting suspension was cooled to 0° C. and T3P 50% w/w solution in ethyl acetate (1.4 mmol) was added drop wise. The reaction mixture was stirred at 0° C. for 1 hour and then warmed to room temperature and stirred for a further hour. An aqueous saturated solution of Na₂CO₃ was added and the mixture stirred for 10 min. Two phases were separated and the organic layer was washed with water and brine, dried over Na₂SO₄ and evaporated to dryness. The residue was purified by flash chromatography on silica gel using cyclohexane/ethyl acetate 80:20 to cyclohexane/ethyl acetate 70:30 as eluents affording the title compound (0.50 g) as white foam.

¹H-NMR (400 MHz, DMSO-d₆): δ ppm 10.08 and 10.03 (1H, br.s), 8.30 (1H, d), 8.03 (1H, dd), 7.00 (1H, d), 6.95-6.90 (2H, m), 6.36 (1H, d), 4.17 (2H, s), 3.98-3.92 (1H, m), 2.10 (3H, s), 1.73-1.52 (2H, m), 1.36 and 1.29 (9H, br.s), 1.23 (6H, s), 0.88 (3H, t). ¹³C-NMR (200 MHz, DMSO-d₆): δ ppm 171.4, 159.0, 158.5, 155.5, 148.9, 138.1, 131.4, 129.8, 125.8, 115.1, 113.9, 110.7, 83.6, 78.0, 56.3, 42.2, 28.9, 26.0, 25.0, 20.7, 14.4, 14.1, 10.5.

Intermediate 31

(2R)-2-amino-N-{6-[(3,3,7-trimethyl-2,3-dihydro-1-benzofuran-4-yl)oxy]-3-pyridinyl}butanamide

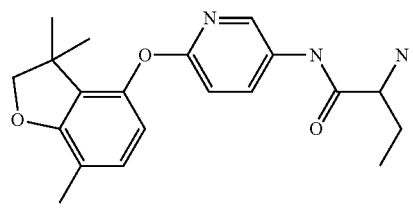 [SMILES: CCC(N)C(=O)Nc1ccc(Oc2ccc(C)c3c2C(C)(C)CO3)nc1]

The 1,1-dimethylethyl {(1R)-[({6-[(3,3,7-trimethyl-2,3-dihydro-1-benzofuran-4-yl)oxy]-3-pyridinyl}amino)carbonyl]propyl}carbamate (Intermediate 30, 480 mg, 1.05 mmol) was dissolved in iso-propyl acetate (5 mL) and HCl 5-6N in isopropanol (1 ml, 5.25 mmol) was added. The solution was stirred at room temperature for 1 hour and then heated to ~50-55° C. until complete conversion. The mixture was cooled to room temperature and treated with an aqueous saturated solution of NaHCO$_3$. Two phases were separated and the organic layer was washed with brine, dried over Na$_2$SO$_4$ and evaporated to dryness. The residue was purified by flash chromatography on silica gel using dichloromethane/methanol 95:5 as eluents affording the title compound (0.31 g) as yellowish foam.

$^1$H-NMR (400 MHz, DMSO-d$_6$): δ ppm 8.36 (1H, d), 8.11 (1H, dd), 6.96-6.92 (2H, m), 6.38 (1H, d), 4.19 (2H, s), 3.23 (1H, dd), 2.11 (3H, s), 1.72-1.61 (1H, m), 1.53-1.43 (1H, m), 1.25 (6H, s), 0.90 (3H, t). $^{13}$C-NMR (200 MHz, DMSO-d$_6$): δ ppm 174.5, 159.0, 158.5, 148.9, 138.2, 131.5, 131.4, 129.8, 125.7, 115.1, 113.9, 110.6, 83.6, 56.7, 42.2, 28.0, 26.0, 14.4, 10.2.

Intermediate 32

5-nitro-2-[(3,3,7-trimethyl-2,3-dihydro-1-benzofuran-4-yl)oxy]pyrimidine

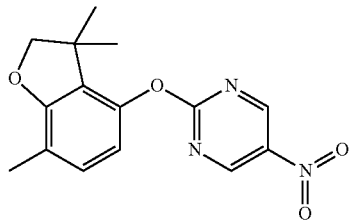 [SMILES: Cc1ccc(Oc2ncc([N+](=O)[O-])cn2)c2c1OCC2(C)C]

3,3,7-Trimethyl-2,3-dihydro-1-benzofuran-4-ol (Intermediate 27, 178 mg, 1.0 mmol) and 2-chloro-5-nitropyrimidine (191.5 mg, 1.2 mmol) were dissolved in CH$_3$CN (3.0 mL) and K$_2$CO$_3$ (345.5 mg, 2.5 mmol) was added. The resulting suspension was heated to 40° C. and stirred for 1 hour. The reaction mixture was then diluted with water (50 mL) and ethyl acetate (50 mL), The organic phase was collected, washed with brine (50 mL) and dried over Na$_2$SO$_4$. The residue was purified by flash chromatography on silica gel using cyclohexane/ethyl acetate 97:3 as eluents affording the title compound (243 mg).

Intermediate 33

2-[(3,3,7-trimethyl-2,3-dihydro-1-benzofuran-4-yl)oxy]-5-pyrimidinamine

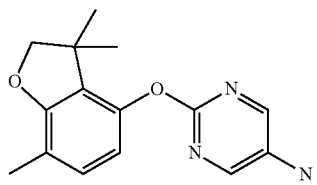 [SMILES: Cc1ccc(Oc2ncc(N)cn2)c2c1OCC2(C)C]

5-nitro-2-[(3,3,7-trimethyl-2,3-dihydro-1-benzofuran-4-yl)oxy]pyrimidine (Intermediate 32, 243 mg, 0.81 mmol) was dissolved in THF (4 mL) and Palladium on charcoal (5 mol %, 85 mg) was added. The reaction mixture was stirred under hydrogen atmosphere (3 bar) for 1 hour at room temperature. The catalyst was filtered on a pad of celite, washed with THF and the resulting solution was concentrated under vacuum. The residue was diluted with ethyl acetate and water, the organic phase collected, dried over Na$_2$SO$_4$ and evaporated to afford the title compound (220 mg) as colorless oil. The crude product, was used in the next step without further purification.

MS 2 (ESI): 272 [M+H]+

Intermediate 34

1,1-dimethylethyl {(1R)-1-[({2-[(3,3,7-trimethyl-2,3-dihydro-1-benzofuran-4-yl)oxy]-5-pyrimidinyl}amino)carbonyl]propyl}carbamate

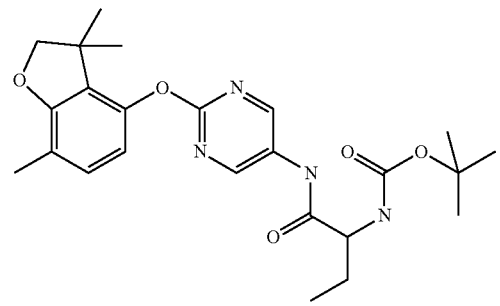 [SMILES: CCC(NC(=O)OC(C)(C)C)C(=O)Nc1cnc(Oc2ccc(C)c3c2C(C)(C)CO3)nc1]

2-[(3,3,7-trimethyl-2,3-dihydro-1-benzofuran-4-yl)oxy]-5-pyrimidinamine (Intermediate 33, 220 mg, 0.81 mmol) was dissolved in ethyl acetate (10 mL) and of (2R)-2-({[(1,1-dimethylethyl)oxy]carbonyl}amino)butanoic acid (181.1 mg, 0.89 mmol) was added followed by the addition of Et$_3$N (0.35 mL, 2.02 mmol). The resulting solution was cooled down to 5° C. and a solution of T3P 50% w/w in ethyl acetate (0.53 mL, 0.89 mmol) was added drop wise in 15 min. The reaction mixture was stirred for 30 min at 5° C. The reaction was quenched with water (50 mL) and ethyl acetate (50 mL), two phases were separated and the organic layer was dried over Na$_2$SO$_4$ and concentrated under vacuum. The residue was purified by flash chromatography on silica gel using cyclohexane/ethyl acetate 60:40 as eluent affording the title compound (213 mg).

MS 2 (ESI):457 [M+H]+.

Intermediate 35

(2,2-difluoro-1,3-benzodioxol-4-yl)boronic acid

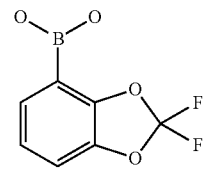 [SMILES: OB(O)c1cccc2c1OC(F)(F)O2]

2,2-Difluoro-1,3-benzodioxole (960 mg, 6.1 mmol) was dissolved in THF (8 mL) and cyclohexane (4 mL) and the resulting solution cooled to −78° C. sec-BuLi 1.4M solution in cyclohexane (4.3 mL, 6.1 mmol) was added dropwise and the reaction mixture stirred for 1.5 hours at −78° C. Trimethylborate (694 mg, 6.75 mmol) was added and the mixture was allowed to warm slowly to −30° C. The reaction mixture was quenched with a 2N solution of HCl and diluted with ethyl acetate. Two phases were separated and the organic layer was washed twice with brine, dried over $Na_2SO_4$ and evaporated to dryness affording the title compound as yellow oil which was used in the next step without further purification.

$^1$H-NMR (400 MHz, DMSO-$d_6$+$D_2O$): δ ppm 7.39 (1H, dd), 7.34 (1H, dd), 7.14 (t, 1H, J=7.90 Hz). $^{19}$F-NMR (376 MHz, DMSO-$d_6$+$D_2O$): δ ppm −48.92. $^{13}$C-NMR (200 MHz, DMSO-$d_6$+$D_2O$): δ ppm 147.3, 142.8, 131.6 (t, J=250.7 Hz), 130.1, 124.3, 112.0

Intermediate 36

(2,2-difluoro-7-methyl-1,3-benzodioxol-4-yl)boronic acid

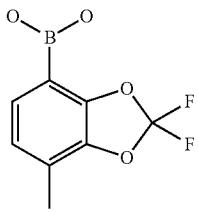

(2,2-difluoro-1,3-benzodioxol-4-yl)boronic acid (Intermediate 35, crude material) was dissolved in THF (20 mL) and the resulting solution cooled down to −78° C. sec-BuLi 1.4M solution in cyclohexane (17.4 ml, 24.36 mmol) was added dropwise and the reaction mixture was stirred for 1.5 hours at −78° C. Methyl iodide (4.6 ml, 73 mmol) was then added and the reaction mixture was stirred for 2 hours while the temperature was allowed to reach room temperature. The reaction was quenched by addition of an aqueous 2N solution of HCl and diluted with ethyl acetate. The organic layer was collected and then washed twice with brine, dried over $Na_2SO_4$ and evaporated to dryness. Crystallization from n-heptane afforded the title compound (150 mg) as white solid.

$^1$H-NMR (400 MHz, DMSO-$d_6$+$D_2O$): δ ppm 7.30 (1H, d), 6.68 (1H, d), 2.25 (s, 3H). $^{19}$F-NMR (376 MHz, DMSO-$d_6$+$D_2O$): δ ppm −48.55. $^{13}$C-NMR (200 MHz, DMSO-$d_6$+$D_2O$): δ ppm 152.5, 147.1, 141.5, 131.6 (t, J=250.0 Hz), 129.9, 125.8, 122.7, 110.1, 14.6.

Intermediate 37

2,2-difluoro-7-methyl-1,3-benzodioxol-4-ol

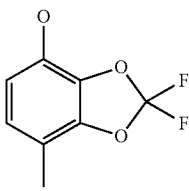

(2,2-difluoro-7-methyl-1,3-benzodioxol-4-yl)boronic acid (Intermediate 36, 150 mg, 1.28 mmol) was dissolved in THF (1.5 mL) and a 30% w/w aqueous solution of $H_2O_2$ (2.56 mmol) and NaOH (51 mg, 1.28 mmol) were added and the reaction mixture stirred for 2 days at room temperature. The reaction was quenched with a 2N aqueous solution of HCl and diluted with ethyl acetate. Two phases were separated and the organic layer was washed twice with brine, dried over $Na_2SO_4$ and evaporated to dryness, affording the title compound (140 mg) as yellow oil.

$^1$H-NMR (400 MHz, DMSO-$d_6$): δ ppm 10.31 (1H, s), 6.83 (1H, d), 6.63 (1H, d), 2.17 (3H, s). $^{19}$F-NMR (376 MHz, DMSO-$d_6$): δ ppm −48.68. $^{13}$C-NMR (200 MHz, DMSO-$d_6$): δ ppm 142.3, 139.1, 131.4 (t, J=251.9 Hz), 129.9, 125.6, 112.8, 110.0, 13.2.

Intermediate 38

2-bromo-3-hydroxyphenyl acetate

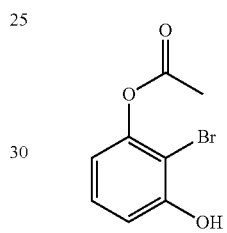

To a solution of 2-bromo-1,3-benzenediol (3.028 g, 16.02 mmol) in dichloromethane (70 ml), TEA (3.35 ml, 24.03 mmol) and acetic anhydride (1.512 ml, 16.02 mmol) were added under stirring. The reaction mixture was stirred at room temperature overnight. The reaction was quenched with a saturated solution of ammonium chloride (100 ml), and extracted with ethyl acetate (3 times 70 ml). The combined organic layers were dried over sodium sulphate, filtered and evaporated to afford the title compound as a black oil which was used directly used in the next step. (3.028 g)

UPLC_B: 0.41 min, 229 [M−H]−

Intermediate 39

2-bromo-3-[(2-methyl-2-propen-1-yl)oxy]phenyl acetate

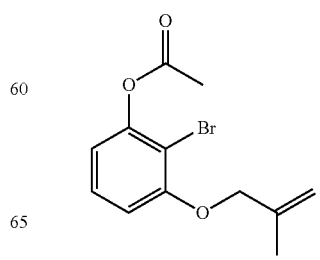

To a solution of 2-bromo-3-hydroxyphenyl acetate (Intermediate 38, 3028 mg) in acetonitrile (60 ml) potassium carbonate (3623 mg, 26.2 mmol) and 3-bromo-2-methyl-1-propene (2123 mg, 15.73 mmol) were added. The reaction mixture was stirred at room temperature overnight. The mixture was washed with water (3 times 60 ml). The organic phase was separated, dried over sodium sulphate, filtered and evaporated. The residue was purified by flash chromatography on silica gel using a 100 g-SNAP column and cyclohexane/ethyl acetate from 100/0 to 80/20 as eluent to afford the title compound as a colourless oil (2.324 g).

$^1$H NMR (400 MHz, CDCl$_3$): δ ppm 7.27 (1H, t), 6.68 (1H, dd), 5.19 (1H, s), 5.04 (1H, s), 4.53 (2H, s), 2.38 (3H, s), 1.88 (3H, s); UPLC: 0.81 min, 285 [M+H]+

Intermediate 40

3,3-dimethyl-2,3-dihydro-1-benzofuran-4-yl acetate

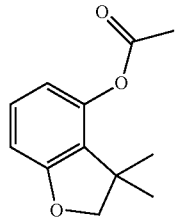

To a solution of 2-bromo-3-[(2-methyl-2-propen-1-yl)oxy]phenyl acetate (Intermediate 39, 2.324 g) in toluene (20 ml) AIBN (1.606 g, 9.78 mmol) and tributylstannane (4.73 g, 16.30 mmol) were added. The reaction mixture was stirred and heated at 100° C. for 2 hours, then was left at room temperature for 4 hours. The reaction was quenched with water (60 ml) and extracted with ethyl acetate (3 times 50 ml). The combined organic layers were dried over sodium sulphate, filtered and evaporated. The residue was purified by flash chromatography on silica gel using a 100 g-SNAP column and cyclohexane/ethyl acetate from 100/0 to 70/30 as eluent to afford the title compound as a colourless oil (1.290 g).

$^1$H NMR (400 MHz, CDCl$_3$): δ ppm 7.13 (1H, t), 6.68 (1H, d), 6.59 (1H, d), 4.22 (2H, s), 2.33 (3H, s), 1.39 (6H, s). UPLC: 0.72 min, 207 [M+H]+

Intermediate 6

3,3-dimethyl-2,3-dihydro-1-benzofuran-4-ol

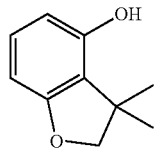

This is an alternative synthetic route to the one described previously for Intermediate 6.

To a solution of 3,3-dimethyl-2,3-dihydro-1-benzofuran-4-yl acetate (Intermediate 40, 1.290 g) in methanol (50 ml) a solution of sodium hydroxide (0.375 g, 9.38 mmol) in water (25.00 ml) was added. The reaction mixture was stirred at room temperature for 30 minutes. The mixture was then acidified with HCl 5% until pH=5 and extracted with ethyl acetate (3 times 50 ml). The combined organic layers were dried over sodium sulphate, filtered and evaporated. The residue was purified by flash chromatography on silica gel using a 25 g-SNAP column and cyclohexane/ethyl acetate from 100/0 to 80/20 as eluent to afford the title compound as a white solid (855 mg).

UPLC: 0.65 min, 165 [M+H]+

Example 1

(5R)-5-ethyl-5-methyl-3-[2-(7-methylspiro[2H-benzofuran-3,1'-cyclopropane]-4-yl)oxypyrimidin-5-yl]imidazolidine-2,4-dione

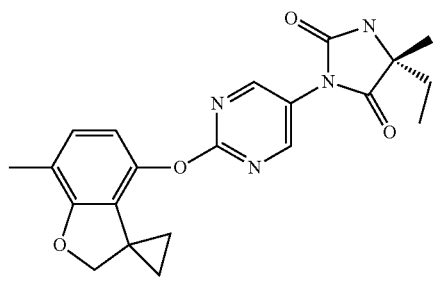 [SMILES: CC[C@@]1(C)NC(=O)N(c2cnc(Oc3ccc(C)c4c3C3(CC3)CO4)nc2)C1=O]

To a solution of 7-methylspiro[2H-benzofuran-3,1'-cyclopropane]-4-ol (Intermediate 13, 18 mg, 0.1 mmol) in dry DMF (1 ml) potassium carbonate (27.6 mg, 0.2 mmol) and then (5R)-3-(2-chloropyrimidin-5-yl)-5-ethyl-5-methyl-imidazolidine-2,4-dione (Intermediate 22, 20 mg, 0.08 mmol) were added and the reaction mixture was stirred for 2 hours at 80° C. After cooling the reaction mixture was quenched with water (1 ml), diluted with brine (5 ml) and extracted with ethyl acetate (2×10 ml). The organic layer was dried over sodium sulfate, filtered and evaporated and the residue was purified by flash chromatography (Biotage system) on silica gel using a 10 g SNAP column and cyclohexane/ethyl acetate 7:3 to cyclohexane/ethyl acetate 3:7 as eluents affording the title compound (21 mg) as a white solid.

$^1$H-NMR (400 MHz, DMSO-d$_6$) δ ppm: 8.69-8.74 (3H, m), 6.94 (1H, d), 6.52 (1H, d), 4.44 (2H, s), 2.15 (3H, s), 1.73-1.83 (1H, m), 1.63-1.73 (1H, m), 1.40 (3H, s), 1.02-1.06 (2H, m), 0.85-0.92 (5H, m). LC/MS: QC 3 MIN: Rt=2.007 min; 395 [M+H]+.

The following compounds were prepared using the foregoing methodology, replacing 7-methylspiro[2H-benzofuran-3,1'-cyclopropane]-4-ol (Intermediate 13) with the appropriate phenol. Final products were purified by flash-chromatography (Silica cartridge; Cyclohexane/EtOAc or other appropriate solvent system).

| Ex. | Structure | Name | Phenol | ¹H-NMR | LCMS |
|---|---|---|---|---|---|
| 2 | 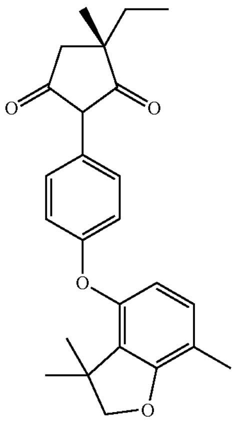 | (5R)-5-ethyl-5-methyl-3-{2-[(3,3,7-trimethyl-2,3-dihydro-1-benzofuran-4-yl)oxy]-5-pyrimidinyl}-2,4-imidazo-lidinedione | 3,3,7-trimethyl-2,3-dihydro-1-benzofuran-4-ol (Inter-mediate 27) | ¹H NMR (400 MHz, DMSO-d$_6$) δ ppm: 8.70 (1H, br.s), 8.69 (2H,s), 6.98 (1H, d), 6.55 (1H, d), 4.19 (2H, s), 2.12 (3H, s), 1.90-1.50 (1H, m), 1.38 (3H, s), 1.21 (6H, s), 0.86 (3H, t). | UPLC: 1.06 min, 397 [M + H]+ |
| 3 | 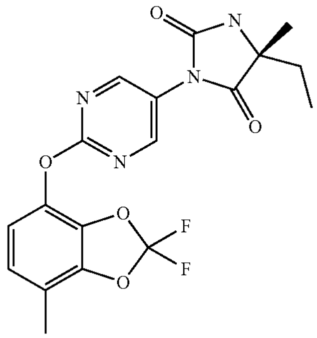 [SMILES: CC[C@@]1(C)NC(=O)N(c2cnc(Oc3ccc(C)c4c3OC(F)(F)O4)nc2)C1=O] | (5R)-3-{2-[(2,2-difluoro-7-methyl-1,3-benzodioxol-4-yl)oxy]-5-pyrimidinyl}-5-ethyl-5-methyl-2,4-imidazo-lidinedione | 2,2-difluoro-7-methyl-1,3-benzodioxol-4-ol (Inter-mediate 37) | ¹H-NMR (400 MHz, DMSO-d$_6$): δ ppm 8.78 (2H, s), 8.74 (1H, br.s), 7.18-7.13 (2H, m), 2.33 (3H, s), 1.84-1.75 (1H, m), 1.71-1.62 (1H, m), 1.40 (3H, s), 0.88 (3H, t. | UPLC: 1.11 min, 407 [M + H]+, |

Example 4

5,5-dimethyl-3-[2-(7-methylspiro[2H-benzofuran-3,1'-cyclopropane]-4-yl)oxypyrimidin-5-yl]imidazoli-dine-2,4-dione

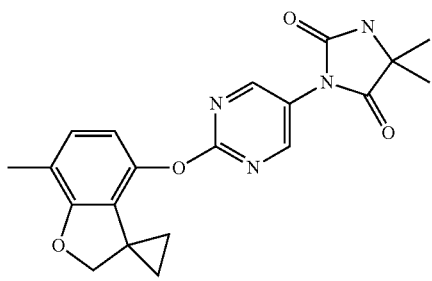

To a solution of 7-methylspiro[2H-benzofuran-3,1'-cyclopropane]-4-ol (Intermediate 13, 18 mg 0.1 mmol) in dry DMF (1 ml) potassium carbonate (27.6 mg, 0.2 mmol) and then 3-(2-chloropyrimidin-5-yl)-5,5-dimethyl-imidazoli-dine-2,4-dione (Intermediate 23, 20 mg, 0.083 mmol) were added and the reaction mixture was stirred for 2 hours at 80° C. After cooling the reaction mixture was quenched with water (1 ml), diluted with brine (5 ml) and extracted with ethyl acetate (2×10 ml). The organic layer was dried over sodium sulfate, filtered and evaporated and the residue was purified by flash chromatography (Biotage system) on silica gel using a 10 g SNAP column and cyclohexane/ethyl acetate 7:3 to cyclohexane/ethyl acetate 3:7 as eluents affording the title compound (18 mg) as a light beige solid.

¹H-NMR (400 MHz, DMSO-d$_6$) δ ppm: 8.74 (1H, s), 8.70 (2H, s), 6.94 (1H, d), 6.52 (1H, d), 4.44 (2H, s), 2.14 (3H, s), 1.42 (6H, s), 1.01-1.06 (2H, m), 0.87-0.92 (2H, m).
LC/MS: QC 3 MIN: Rt=1.946 min; 380 [M+H]+.

Example 5

(5R)-5-ethyl-3-[2-(7-methylspiro[2H-benzofuran-3,1'-cyclopropane]-4-yl)oxypyrimidin-5-yl]imidazoli-dine-2,4-dione

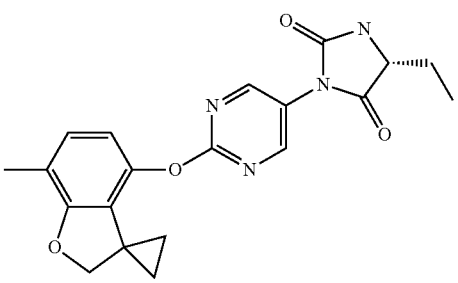 [SMILES: CC[C@H]1NC(=O)N(c2cnc(Oc3ccc(C)c4c3C3(CC3)CO4)nc2)C1=O]

To a solution of (2R)-2-amino-N-[2-(7-methylspiro[2H-benzofuran-3,1'-cyclopropane]-4-yl)oxypyrimidin-5-yl]bu-tanamide (Intermediate 21, 24 mg, 0.068 mmol) in dry DCM (3 ml) TEA (0.028 ml, 0.2 mmol) was added and the reaction mixture was cooled to 0° C. A solution of triphosgene (15 mg, 0.05 mmol) in dry DCM (1.5 ml) was slowly added and the reaction mixture was stirred for 15 minutes at the same temperature. The reaction was quenched with water (10 ml) and two phases were separated. The organic layer was dried (Na$_2$SO$_4$), filtered and evaporated and the residue was purified purified by flash chromatography (Biotage system)

on silica gel using a 10 g SNAP column and cyclohexane/ethyl acetate 75:25 to cyclohexane/ethyl acetate 25:75 as eluents affording the title compound (11 mg) as a white solid.

¹H-NMR (400 MHz, DMSO-d₆) δ ppm: 8.75 (1H, s), 8.68 (2H, s), 6.94 (1H, d), 6.52 (1H, d), 4.44 (2H, s), 4.20-4.25 (1H, m), 2.15 (3H, s), 1.77-1.88 (1H, m), 1.66-1.76 (1H, m), 1.02-1.06 (2H, m), 0.96 (3H, t), 0.87-0.92 (2H, m). LC/MS: QC 3 MIN: Rt=1.955 min; 381 [M+H]+.

Example 6

(5R)-5-ethyl-3-[6-(7-methylspiro[2H-benzofuran-3,1'-cyclopropane]-4-yl)oxy-3-pyridyl]imidazolidine-2,4-dione

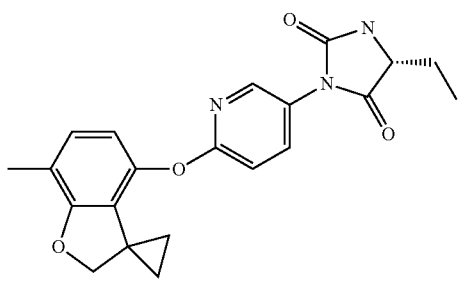 [SMILES: CC[C@H]1NC(=O)N(c2ccc(Oc3ccc(C)c4c3C3(CC3)CO4)nc2)C1=O]

To a solution of (2R)-2-amino-N-[6-(7-methylspiro[2H-benzofuran-3,1'-cyclopropane]-4-yl)oxy-3-pyridyl]butanamide (Intermediate 17, 40 mg, 0.11 mmol) in dry DCM (5 ml) TEA (0.042 ml, 0.3 mmol) was added and the reaction mixture was cooled to 0° C. A solution of triphosgene (23.7 mg, 0.08 mmol) in dry DCM (3 ml) was slowly added and the reaction mixture was stirred for 15 minutes at the same temperature. The reaction was quenched with water (10 ml) and two phases were separated. The organic layer was dried (Na₂SO₄), filtered and evaporated and the residue was purified purified by flash chromatography (Biotage system) on silica gel using a 10 g SNAP column and cyclohexane/ethyl acetate 75:25 to cyclohexane/ethyl acetate 25:75 as eluents affording the title compound (22 mg) as a white solid.

¹H-NMR (400 MHz, DMSO-d₆) δ ppm: 8.63 (1H, s), 8.13 (1H, d), 7.84 (1H, dd), 7.07 (1H, d), 6.94 (1H, d), 6.44 (1H, d), 4.46 (2H, s), 4.19-4.24 (1H, m), 2.15 (3H, s), 1.77-1.88 (1H, m), 1.65-1.75 (1H, m), 1.10-1.14 (2H, m), 0.96 (3H, t), 0.87-0.92 (2H, m).

LC/MS: QC 3 MIN: Rt=2.025 min; 380 [M+H]+.

Example 7

(5R)-5-ethyl-3-{6-[(3,3,7-trimethyl-2,3-dihydro-1-benzofuran-4-yl)oxy]-3-pyridinyl}-2,4-imidazolidinedione

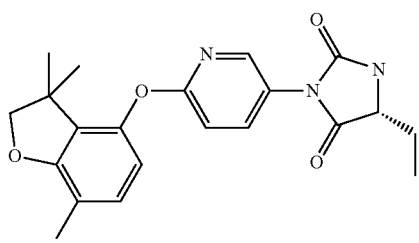 [SMILES: CC[C@H]1NC(=O)N(c2ccc(Oc3ccc(C)c4c3C(C)(C)CO4)nc2)C1=O]

(2R)-2-amino-N-{6-[(3,3,7-trimethyl-2,3-dihydro-1-benzofuran-4-yl)oxy]-3-pyridinyl}butanamide (Intermediate 31, 300 mg, 0.84 mmol) was dissolved in ethyl acetate (6 mL). Triethylamine (0.47 ml, 3.36 mmol) was added and the reaction mixture was cooled to 0° C. A solution of triphosgene (100 mg, 0.34 mmol) in ethyl acetate (6 mL) was slowly added. At the end of addition the mixture was treated with an aqueous saturated solution of NaHCO₃ and two phases were separated. The organic layer was washed with brine, dried over Na₂SO₄ and evaporated to dryness to obtain a waxy solid. The residue was purified purified by flash chromatography on silica gel using cyclohexane/ethyl acetate 70:30 to cyclohexane/ethyl acetate 50:50 as eluents affording the title compound (166 mg) as a white foam.

¹H-NMR (400 MHz, DMSO-d₆): δ ppm 8.61 (1H, br.s), 8.12 (1H, d), 7.82 (1H, dd), 7.10 (1H, d), 6.98 (1H, d), 6.47 (1H, d), 4.21 (2H, s), 4.18 (1H, br.s), 2.13 (3H, s), 1.86-176 (1H, m), 1.75-1.64 (1H, m), 1.25 (6H, s), 0.95 (3H, t).
¹³C-NMR (200 MHz, DMSO-d₆): δ ppm 173.2, 162.5, 158.6, 155.4, 148.2, 145.2, 138.5, 130.0, 126.1, 124.3, 115.7, 114.4, 110.6, 83.6, 57.5, 42.2, 26.0, 24.4, 14.4, 8.8.

Example 8

(5R)-5-ethyl-3-{2-[(3,3,7-trimethyl-2,3-dihydro-1-benzofuran-4-yl)oxy]-5-pyrimidinyl}-2,4-imidazolidinedione

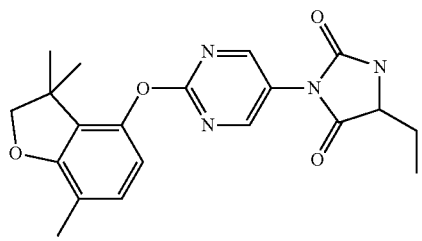 [SMILES: CCC1NC(=O)N(c2cnc(Oc3ccc(C)c4c3C(C)(C)CO4)nc2)C1=O]

1,1-dimethylethyl {(1R)-1-[({2-[(3,3,7-trimethyl-2,3-dihydro-1-benzofuran-4-oxy]-5-pyrimidinyl}amino)carbonyl]propyl}carbamate (Intermediate 34, 213 mg, 0.47 mmol) was dissolved in HCl 5-6 N in isopropanol (1 mL) and the resulting solution was heated to 35° C. for 30 minutes. The reaction mixture was then concentrated under vacuum, the residue diluted with ethyl acetate (50 mL) and an aqueous 5% solution of K₂CO₃ (30 mL). Two phases were separated and the organic layer was washed with an aqueous saturated solution of ammonium chloride (30 mL), dried over Na₂SO₄ and concentrated under vacuum. The resulting crude was dissolved in ethyl acetate (10 mL) and triethylamine was added (0.23 mL, 1.64 mmol). The reaction mixture was cooled to 0-5° C. and a solution of triphosgene (55 mg, 0.185 mmol) in ethyl acetate (5 mL) was added drop wise in 10 minutes. The reaction was quenched with water (50 mL) and extracted with ethyl acetate (50 mL). The organic layer was washed with brine dried over Na₂SO₄ and concentrated under vacuum. The residue was purified purified by flash chromatography on silica gel using cyclohexane/ethyl acetate 50:50 as eluent affording the title compound (161 mg) as a white solid.

¹H NMR (400 MHz, DMSO-d₆): δ ppm 8.72 (1H, s), 8.66 (2H, s), 7.03-6.93 (1H, m), 6.55 (1H, d), 4.18 (2H, s), 2.12 (3H, s), 1.87-1.61 (2H, m), 1.2 (6H, s), 1.15 (1H, t), 0.94 (3H, t). MS 2 (ESI): 383 [M+H].

Example 9

(5R)-5-ethyl-5-methyl-3-[6-(7-methylspiro[2H-benzofuran-3,1'-cyclopropane]-4-yl)oxy-3-pyridyl]imidazolidine-2,4-dione

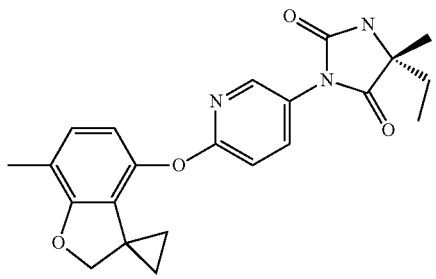 [SMILES: CC[C@@]1(C)NC(=O)N(c2ccc(Oc3ccc(C)c4c3C3(CC3)CO4)nc2)C1=O]

To a solution of triphosgene (30 mg, 0.1 mmol) in dry DCM (1 ml) at 0° C., under nitrogen atmosphere, DIPEA (0.175 ml, 1.0 mmol) was added followed by the addition (slowly added) of a solution of 6-(7-methylspiro[2H-benzofuran-3,1'-cyclopropane]-4-yl)oxypyridin-3-amine (Intermediate 15, 27 mg, 0.1 mmol) in dry DCM (2 ml) and the reaction mixture was stirred for 15 minutes at the same temperature. After that a solution of Methyl (R)-2-amino-2-methyl-butyrate hydrochloride (33 mg, 0.2 mmol) in dry DCM (2 ml) was added and the reaction mixture was stirred for 30 minutes at 0° C. The reaction was quenched with a 1M aqueous solution of HCl (5 ml), diluted with DCM (10 ml) and two phases were separated. The organic layer was washed with brine (10 ml), dried ($Na_2SO_4$), filtered and evaporated affording the urea intermediate as yellow foam.

The urea was dissolved in MeOH (5 ml), NaOMe (10 mg) was added and the reaction mixture was stirred for 15 minutes at room temperature. The reaction was quenched with an aqueous saturated solution of ammonium chloride (20 ml) and diluted with ethyl acetate (40 ml). Two phases were separated and the organic layer was dried ($Na_2SO_4$), filtered and evaporated and the residue was purified by flash chromatography (Biotage system) on silica gel using a 10 g SNAP column and cyclohexane/ethyl acetate 75:25 to cyclohexane/ethyl acetate 25:75 as eluents affording the title compound (29 mg) as a white solid.

$^1$H-NMR (400 MHz, DMSO-$d_6$) δ ppm: 8.60 (1H, s), 8.15 (1H, d), 7.85 (1H, dd), 7.06 (1H, d), 6.94 (1H, d), 6.44 (1H, d), 4.46 (2H, s), 2.15 (3H, s), 1.73-1.83 (1H, m), 1.62-1.72 (1H, m), 1.40 (3H, s), 1.10-1.14 (2H, m), 0.84-0.92 (5H, m). LC/MS: QC 3 MIN: Rt=2.076 min; 394 [M+H]+.

Example 10

5,5-dimethyl-3-[6-(7-methylspiro[2H-benzofuran-3,1'-cyclopropane]-4-yl)oxy-3-pyridyl]imidazolidine-2,4-dione

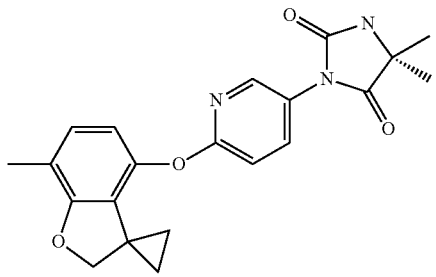

To a solution of triphosgene (30 mg, 0.1 mmol) in dry DCM (1 ml) at 0° C., under nitrogen atmosphere, DIPEA (0.175 ml, 1.0 mmol) was added followed by the addition (slowly added) of a solution of 6-(7-methylspiro[2H-benzofuran-3,1'-cyclopropane]-4-yl)oxypyridin-3-amine (Intermediate 15, 27 mg, 0.1 mmol) in dry DCM (2 ml) and the reaction mixture was stirred for 15 minutes at the same temperature. After that a solution of Methyl 2-amino-2-methylpropanoate hydrochloride (30 mg, 0.2 mmol) in dry DCM (2 ml) was added and the reaction mixture was stirred for 30 minutes at 0° C. The reaction was quenched with a 1M aqueous solution of HCl (5 ml), diluted with DCM (10 ml) and two phases were separated. The organic layer was washed with brine (10 ml), dried ($Na_2SO_4$), filtered and evaporated affording the urea intermediate as yellow foam.

The urea was dissolved in MeOH (5 ml), NaOMe (10 mg, 0.19 mmol) was added and the reaction mixture was stirred for 15 minutes at room temperature. The reaction was quenched with an aqueous saturated solution of ammonium chloride (20 ml) and diluted with ethyl acetate (40 ml). Two phases were separated and the organic layer was dried ($Na_2SO_4$), filtered and evaporated and the residue was purified by flash chromatography (Biotage system) on silica gel using a 10 g SNAP column and cyclohexane/ethyl acetate 75:25 to cyclohexane/ethyl acetate 25:75 as eluents affording the title compound (23 mg) as a white solid.

$^1$H-NMR (400 MHz, DMSO-$d_6$) δ ppm: 8.62 (1H, s), 8.14 (1H, d), 7.86 (1H, dd), 7.05 (1H, d), 6.92 (1H, d), 6.43 (1H, d), 4.44 (2H, s), 2.14 (3H, s), 1.40 (6H, s), 1.08-1.13 (2H, m), 0.96 (3H, t), 0.85-0.90 (2H, m). LC/MS: QC_3_MIN: Rt=2.016 min; 380 [M+H]+.

The following Reference Examples were prepared as described in WO2012/076877:

Reference Example RE1

(5R)-5-ethyl-3-(6-{[4-methyl-3-(methyloxy)phenyl]oxy}-3-pyridinyl)-2,4-imidazolidinedione

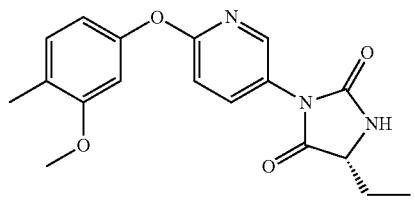 [SMILES: CC[C@H]1NC(=O)N(c2ccc(Oc3ccc(C)c(OC)c3)nc2)C1=O]

Reference Example RE2

(5R)-5-ethyl-5-methyl-3-(6-{[4-methyl-3-(methyloxy)phenyl]oxy}-3-pyridinyl)-2,4-imidazolidinedione

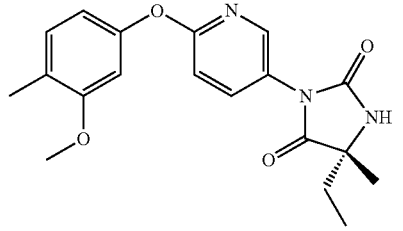

Reference Example RE3

3-(1,1-dimethylethyl)-4-({5-[(4R)-4-ethyl-2,5-dioxo-1-imidazolidinyl]-2-pyridinyl}oxy)benzonitrile

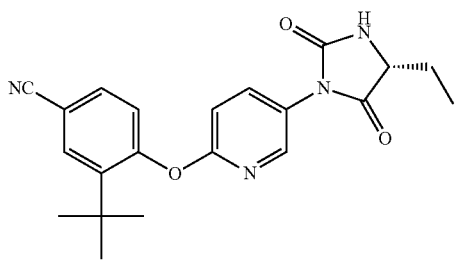 [SMILES: CC[C@H]1NC(=O)N(c2ccc(Oc3ccc(C#N)cc3C(C)(C)C)nc2)C1=O]

Reference Example RE4

4-({5-[(4R)-4-ethyl-2,5-dioxo-1-imidazolidinyl]-2-pyridinyl}oxy)-2-(1-methylethyl)benzonitrile

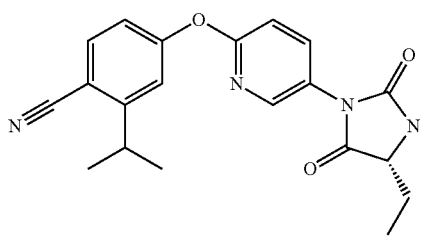 [SMILES: CC[C@H]1NC(=O)N(c2ccc(Oc3ccc(C#N)c(C(C)C)c3)nc2)C1=O]

Reference Example RE5

3-cyclopropyl-4-({5-[(4R)-4-ethyl-2,5-dioxo-1-imidazolidinyl]-2-pyridinyl}oxy)benzonitrile

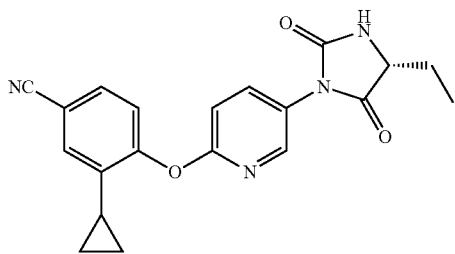 [SMILES: CC[C@H]1NC(=O)N(c2ccc(Oc3ccc(C#N)cc3C3CC3)nc2)C1=O]

Reference Example RE6

4-({5-[(4R)-4-ethyl-2,5-dioxo-1-imidazolidinyl]-2-pyridinyl}oxy)-2-(1-methylethyl)benzonitrile

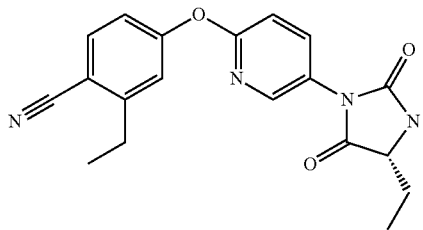 [SMILES: CCc1cc(Oc2ccc(N3C(=O)N[C@H](CC)C3=O)cn2)ccc1C#N]

Reference Example RE7

4-({5-[(4R)-4-ethyl-2,5-dioxo-1-imidazolidinyl]-2-pyridinyl}oxy)-2-[(trifluoromethyl)oxy]benzonitrile

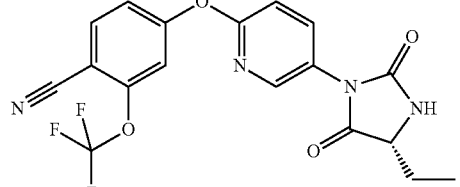

Reference Example RE8

4-({5-[(4R)-4-ethyl-2,5-dioxo-1-imidazolidinyl]-2-pyridinyl}oxy)-2-[(1-methylethyl)oxy]benzonitrile

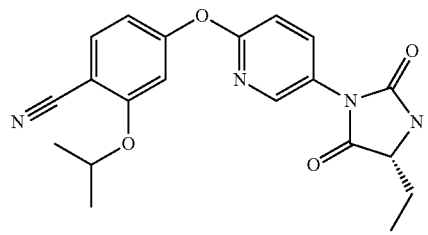 [SMILES: CC[C@H]1NC(=O)N(c2ccc(Oc3ccc(C#N)c(OC(C)C)c3)nc2)C1=O]

Reference Example RE9

(5R)-5-ethyl-3-[6-(spiro[1-benzofuran-3,1'-cyclopropan]-4-yloxy)-3-pyridinyl]-2,4-imidazolidinedione

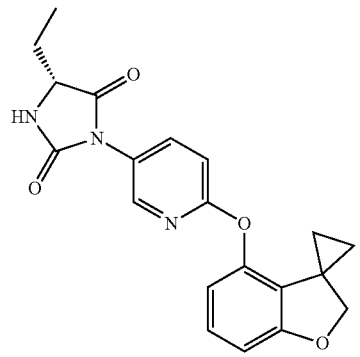 [SMILES: CC[C@H]1NC(=O)N(c2ccc(Oc3cccc4c3C3(CC3)CO4)nc2)C1=O]

Reference Example RE10

5,5-dimethyl-3-[6-(spiro[1-benzofuran-3,1'-cyclopropan]-4-yloxy)-3-pyridinyl]-2,4-imidazolidinedione

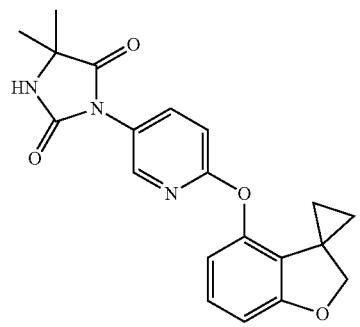 [SMILES: CC1(C)NC(=O)N(c2ccc(Oc3cccc4c3C3(CC3)CO4)nc2)C1=O]

Biological Example 1

The ability of the compounds of the invention to modulate the voltage-gated potassium channel subtypes Kv3.2 or Kv3.1 may be determined using the following assay. Analogous methods may be used to investigate the ability of the compounds of the invention to modulate other channel subtypes, including Kv3.3 and Kv3.4.

Cell Biology

To assess compound effects on human Kv3.2 channels (hKv3.2), a stable cell line expressing hKv3.2 was created by transfecting Chinese Hamster Ovary (CHO)-K1 cells with a pCIH5-hKv3.2 vector. Cells were cultured in DMEM/F12 medium supplemented by 10% Foetal Bovine Serum, 1X non-essential amino acids (Invitrogen) and 500 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pCDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

Cell Preparation for Ion Works Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. From the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. Test pulses protocol may be performed in the absence (pre-read) and presence (post-read) of the test compound. Pre- and post-reads may be separated by the compound addition followed by a 3 minute incubation.

Solutions and Drugs

The intracellular solution contained the following (in mM): K-gluconate 100, KCl 54, $MgCl_2$ 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): $CaCl_2$ 0.90, KCl 2.67, $KH_2PO_4$ 1.47, $MgCl_2 \cdot 6H_2O$ 0.493, NaCl 136.9, $Na_3PO_4$ 8.06, with a pH of 7.4.

Compounds of the invention (or reference compounds such as N-cyclohexyl-N-[(7,8-dimethyl-2-oxo-1,2-dihydro-3-quinolinyl)methyl]-N'-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 μL) was transferred to another compound plate and external solution containing 0.05% pluronic acid (66 μL) was added. 3.5 μL from each plate containing a compound of the invention was added and incubated with the cells during the IonWorks Quattro™ experiment. The final assay dilution was 200 and the final compound concentrations were in the range 50 μM to 50 nM.

Data Analysis

The recordings were analysed and filtered using both seal resistance (>20 MΩ) and peak current amplitude (>500 pA at the voltage step of 40 mV) in the absence of compound to eliminate unsuitable cells from further analysis. Paired comparisons between pre- and post-drug additions measured for the −15 mV voltage step were used to determine the positive modulation effect of each compound. Kv3 channel-mediated outward currents were measured determined from the mean amplitude of the current over the final 10 ms of the −15 mV voltage pulse minus the mean baseline current at −70 mV over a 10 ms period just prior to the −15 mV step. These Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound (EC50) was determined by fitting of the concentration-response data using a four parameter logistic function with ActivityBase or XL-fit software.

N-cyclohexyl-N-[(7,8-dimethyl-2-oxo-1,2-dihydro-3-quinolinyl)methyl]-N'-phenylurea was obtained from ASINEX (Registry Number: 552311-06-5).

All of the Example compounds were tested in the above assay measuring potentiation of Kv3.1 or Kv3.2 or Kv3.1 and Kv3.2 (herein after "Kv3.1 and/or Kv3.2"). Kv3.1 and/or Kv3.2 positive modulators produce in the above assay an increase of whole-cell currents of, on average, at least 20% of that observed with 50 microM N-cyclohexyl-N-[(7,8-dimethyl-2-oxo-1,2-dihydro-3-quinolinyl)methyl]-N'-phenylurea. Thus, in the recombinant cell assays of Biological Example 1, all of the Example compounds act as positive modulators of Kv3.1 and Kv3.2 channels. As used herein, a Kv3.1 and/or Kv3.2 positive modulator is a compound which has been shown to produce at least 20% potentiation of whole-cell currents mediated by human Kv3.1 and/or human Kv3.2 channels recombinantly expressed in mammalian cells, as determined using the assays described in Biological Example 1 (Biological Assays).

A secondary analysis of the data from the assays described in Biological Example 1 may be used to investigate the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1 or Kv3.2 currents following the start of the −15 mV depolarising voltage pulse.

$$Y=(Y0-Y\max)*\exp(-K*X)+Y\max$$

where:

Y0 is the current value at the start of the depolarising voltage pulse;

Ymax is the plateau current;

K is the rate constant, and $Tau_{act}$ is the activation time constant, which is the reciprocal of K.

Similarly, the effect of the compounds on the time taken for Kv3.1 and Kv3.2 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

The time constant for activation ($Tau_{act}$) has been determined for all of the compounds of the Examples. FIG. 1 shows the data for two compounds. Table 1 provides the $Tau_{act}$ data for all of the Examples analysed in this way.

FIG. 1a shows hKv3.2 currents recorded using the assay described in Biological Example 1. Data shown are the individual currents over the period of the depolarising voltage step to −15 mV recorded from 4 different cells at two concentrations of compound (Reference Example RE1). The data are fitted by a single exponential curve (solid lines) using the fitting procedure in Prism version 5 (Graphpad Software Inc).

Figure 1B:
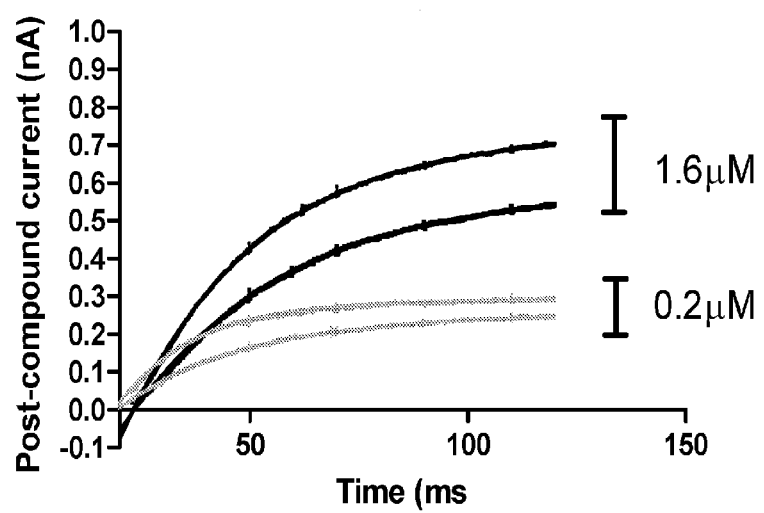
FIG. 1B hKv3.2 currents recorded using the assay described in Biological Example 1. Data shown are the individual currents over the period of the depolarising voltage step to −15 mV recorded from 2 different cells at two concentrations of compound of Reference Example RE3. The data are fitted by a single exponential curve (solid lines) using the fitting procedure in Prism version 5 (Graphpad Software Inc).

FIG. 1b shows hKv3.2 currents recorded using the assay described in Biological Example 1. Data shown are the individual currents over the period of the depolarising voltage step to −15 mV recorded from 2 different cells at two concentrations of the compound of Reference Example RE3. The data are fitted by a single exponential curve (solid lines) using the fitting procedure in Prism version 5 (Graphpad Software Inc).

TABLE 1

Summary hKv3.2 data from the analysis of activation time ($Tau_{act}$).
To allow for comparison between compounds, the compound
concentration chosen was that which produced a similar current
(~0.3 nA) at the end of the voltage pulse, with the exception
of the vehicle, where maximum currents were <0.1 nA.

| Example | Concentration (μM) | $Tau_{act}$ mean (ms) | Standard Deviation | Number of experiments |
| --- | --- | --- | --- | --- |
| Vehicle | — | 7.1 | 1.7 | 6 (cells) |
| RE1 | 6.25 | 9.9 | 2.2 | 5 |
| RE2 | 12.5 | 7.3 | 1.8 | 4 |
| RE3 | 0.2 | 23.0 | 6.2 | 4 |
| RE4 | 0.8 | 9.2 | 2.3 | 2 |
| RE5 | 3.1 | 13.0 | 2.3 | 2 |
| RE6 | 3.1 | 8.2 | 2.0 | 2 |
| RE7 | 3.1 | 10.4 | 2.8 | 2 |
| RE8 | 3.1 | 9.7 | 1.0 | 2 |
| RE9 | 0.2 | 50.1 | 7.5 | 5 |
| RE10 | 0.4 | 19.3 | 1.0 | 4 |
| Example 9 | 0.8 | 24.0 | 3.6 | 2 |
| Example 6 | 0.4 | 34.8 | 4.9 | 2 |
| Example 5 | 0.8 | 31.5 | 4.0 | 2 |
| Example 1 | 1.6 | 21.3 | 0.1 | 2 |
| Example 2 | 1.6 | 14.8 | 1.9 | 2 |
| Example 7 | 0.4 | 28.0 | 0.4 | 2 |
| Example 8 | 1.6 | 25.0 | 2.1 | 2 |
| Example 4 | 1.6 | 13.1 | 0.7 | 4 |
| Example 3 | 25.0 | 8.9 | 1.0 | 2 |
| Example 10 | 1.6 | 17.3 | 0.7 | 2 |

As can be seen from Table 1, in the absence of compound and presence of vehicle the $Tau_{act}$ was 7.1±1.7 msec. A range of $Tau_{act}$ values (7.3-50.1 msec) was observed in the presence of the test compounds when each was tested at a concentration that increased the Kv3.2 current to a similar level (~0.3 nA).

Kv3.1 and Kv3.2 channels must activate and deactivate very rapidly in order to allow neurons to fire actions potentials at high frequency (Rudy and McBain, 2001, Trends in Neurosciences 24, 517-526). Slowing of activation is likely to delay the onset of action potential repolarisation; slowing of deactivation could lead to hyperpolarising currents that reduce the excitability of the neuron and delay the time before the neuron can fire a further action potential. Together these slowing effects on channel activation and deactivation are likely to lead to a reduction rather than a facilitation of the neurons ability to fire at high frequencies. Thus compounds that have this slowing effect on the Kv3.1 and/or Kv3.2 channels may slow neuronal firing. This slowing of neuronal firing by a compound, such as Reference Example 9 which markedly increases $Tau_{act}$ to 50.1±7.5 msec (Table 1), can be observed from recordings made from "fast-firing" interneurons in the cortex of rat brain, using electrophysiological techniques, in vitro. As can be observed in FIG. 2, the addition of Reference Example 9 reduces the ability of the neurons to fire in response to trains of depolarising pulses at 300 Hz.

Figure 2:
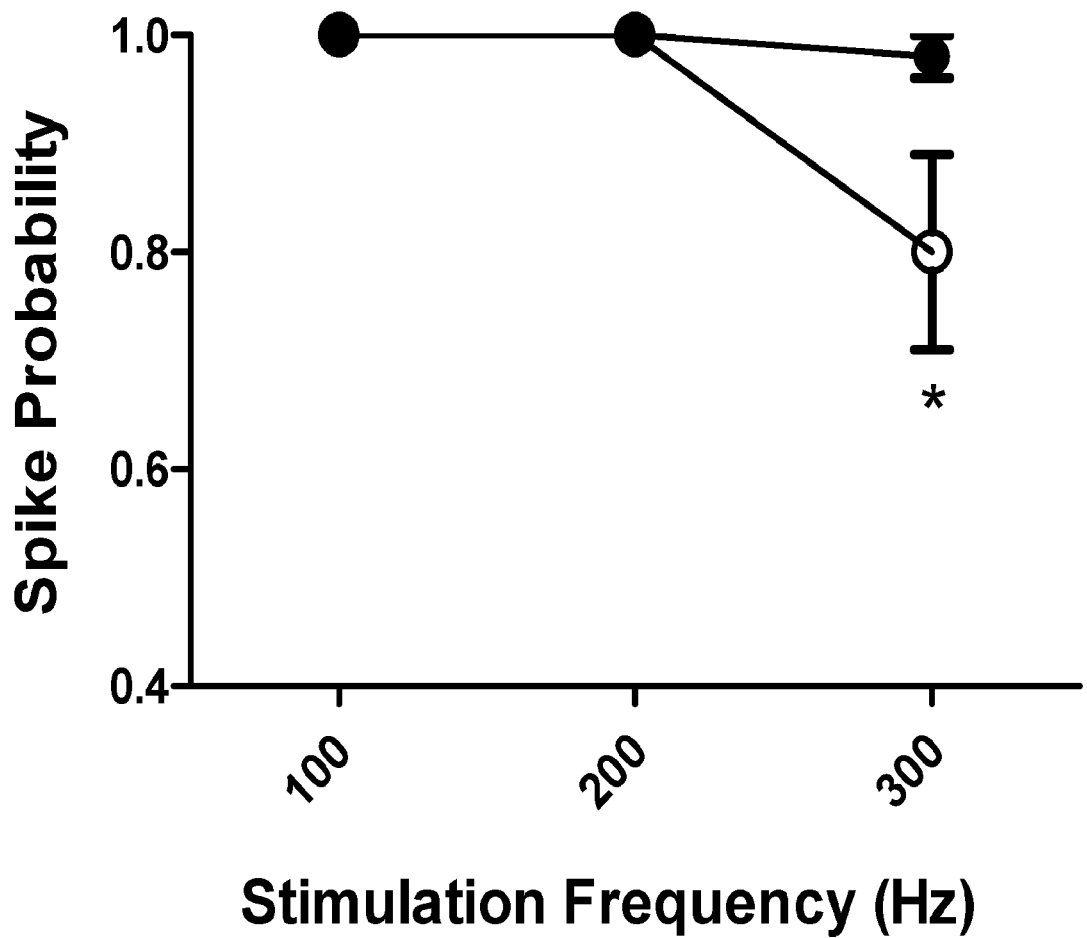
FIG. 2 Recordings made from identified "fast-firing" interneurons in the somatosensory cortex of the mouse.

FIG. 2 shows recordings made from identified "fast-firing" interneurons in the somatosensory cortex of the mouse. The neurons are induced to fire at high frequencies by trains of high frequency depolarising current pulses at 100, 200, and 300 Hz. The ability of the neuron to fire an action potential on each pulse is determined. A spike probability of 1 on the y-axis of the graph indicates that an action potential is generated by the neuron on each of the depolarising current pulses. In the absence of drug (closed circles, n=9), the neurons maintained a spike probability of 1 up to 300 Hz. However, in the presence of Reference Example 9

(1 microM; open circles, n=6), the neurons were unable to follow trains at the highest frequency. * p<0.05, ANOVA for repeated measures.

Therefore, although all the Examples herein identified act as positive modulators in the recombinant cell assay of Biological Example 1, those compounds which markedly increase the value of $Tau_{act}$, may reduce the ability of neurons in native tissues to fire at high frequency.

Biological Example 2

Psychostimulant-Induced Hyperactivity in Mice

Experimental Preparation

Male CD-1 mice (25-35 g) were supplied by Charles River, Italy. Animals were group housed with free access to food (Standard rodent chow) and water under a 12 h light/dark cycle (lights on at 0600 h). A period of at least 5 days between arrival and the study was allowed in all cases.

Experimental Protocol

Animals were administered a test compound at the appropriate dose, route and pre-treatment time, and then returned to their home cage. Testing occurred in a separate room from that used for housing. Mice were treated with the test compound and placed individually into a Perspex box (length 20.5 cm, width 20.5 cm, height 34 cm) covered with a perforated lid. Infrared monitoring sensors were located around the perimeter walls (horizontal sensors). Two additional sensors were located 2.5 cm above the floor on opposite sides (vertical sensors). Data were collected and analysed using a VersaMax System (Accuscan Instruments Inc., Columbus, Ohio) which in turn transferred information to a computer. After 30 minutes of habituation to the test arena, mice were treated with amphetamine (2 mg/kg) dosed intraperitoneally (i.p.) at 10 mL/kg, and subsequent locomotor activity in the test arena was assessed over a further 60 minutes. Locomotor activity in the horizontal plane was determined from the number of interruptions of the horizontal sensors by each mouse in the test arena over the 60 minute test period.

Drugs and Materials

All doses were calculated as base. Clozapine was dissolved in distilled water and dosed at 3 mg/kg intraperitoneum (i.p.) at 10 mL/kg. Example 4 (3, 10, or 30 mg/kg) or vehicle (Captisol 20%+Tween 80 0.1% and HPMC 0.5% in sterile water) was administered i.p. at 10 mL/kg. Both clozapine and Example 4 were dosed immediately before placing the animal in the test arena (30 minutes before amphetamine administration).

Analysis of Blood Levels of Example 4

Blood samples were collected from a subset of study mice (n=3) at the end of the behavioural measurement (90 minutes post-dose of test drug), and assayed using a method based on protein precipitation with acetonitrile followed by HPLC-MS/MS analysis with an optimized analytical method. Since the stability of the analyte in blood and brain was unknown, Calibration standards (CS) and Quality control samples (QC) were prepared on the day of dosing and stored together with study samples. Study samples, CS, QC and blanks were spiked with rolipram as internal standard (IS). Study samples were analyzed in discrete batches together with CS, QC and blank samples.

Results

Amphetamine alone produced a large and significant increase in total locomotor activity. A dose of 10 mg/kg i.p. of Example 4 significantly reduced the increase in total locomotor activity produced by amphetamine. A higher dose of 30 mg/kg i.p. of Example 4 further reduced the increase in locomotor activity induced by amphetamine in a manner similar to the positive control, clozapine (3 mg/kg i.p.). Data are summarised in Table 1.

TABLE 1

Effects of Example 4 on amphetamine induced hyperlocomotion in the mouse. Example 4 was administered i.p. 30 minutes before amphetamine (2 mg/kg i.p.). Clozapine was administered i.p. 30 minutes before amphetamine (2 mg/kg i.p.). Locomotor activity was assessed over 60 minutes starting immediately after amphetamine administration. Data are expressed as mean ± sem. Data were subjected to one-way analysis of variance (ANOVA) followed by Dunnett's test (***p < 0.001, *p < 0.05 vs amphetamine treatment alone). Blood concentrations were determined from a subset of 3 mice at the end of the experiment, 90 minutes after test drug administration. Data shown are the mean blood concentrations and range. (n.d. = not determined).

| Treatment | Locomotor activity (beam crosses) | Blood concentration of Test Drug (ng/mL) |
|---|---|---|
| Vehicle | 5116 ± 1040*** | n.d. |
| Amphetamine (AMPH) 2.0 mg/kg | 16190 ± 2394 | n.d. |
| AMPH 2 mg/kg + Example 4 3 mg/kg | 10263 ± 2443 | 98 [34-168] |
| AMPH 2 mg/kg + Example 4 10 mg/kg | 9015 ± 1413* | 244 [215-300] |
| AMPH 2 mg/kg + Example 4 30 mg/kg | 4555 ± 922*** | 2140 [1790-2380] |
| AMPH 2 mg/kg + Clozapine mg/kg | 1546 ± 420*** | n.d. |

CONCLUSIONS

These results show that Example 4 is able to prevent hyperactivity induced by the psychostimulant, amphetamine. Thus, Example 4 and other compounds that positively modulate Kv3.1 and/or Kv3.2 channels, in the absence of effects on channels gating kinetics, as can be observed from the assay described in Biological Example 1, may be useful in the treatment of disorders associated with hyperactivity, such as bipolar mania, or disruption of the dopamine system, such that may occur in drug dependence, attention deficit hyperactivity disorder (ADHD), or schizophrenia.

Further illustrations of the potential utility of compounds of the present invention are provided, for example, in WO2012/076877 which associates the use of Kv3.1 and/or Kv3.2 channel modulators with a number of disorders.

We claim:

1. A method for the treatment of schizophrenia, which comprises administering to a subject in need thereof a compound of formula (I):

5,5-dimethyl-3-[2-(7-methylspiro[2H-benzofuran-3,1'-cyclopropane]-4-yl)oxypyrimidin-5-yl]imidazolidine-2,4-dione

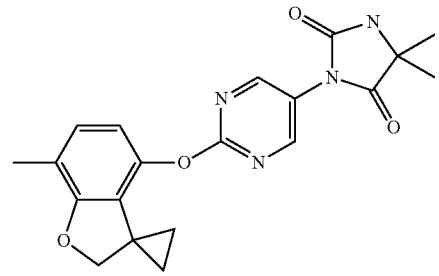

or a pharmaceutically acceptable salt and/or solvate thereof.

* * * * *